| (12) United States Patent | (10) Patent No.: US 7,569,694 B2 |
| Koike et al. | (45) Date of Patent: Aug. 4, 2009 |

(54) COUMARIN COMPOUND, MATERIAL FOR LIGHT EMITTING DEVICE AND ORGANIC ELECTROLUMINESCENT DEVICE

(75) Inventors: Toshihiro Koike, Ichihara (JP); Manabu Uchida, Ichihara (JP); Makoto Satsuki, Okayama (JP); Makoto Fujiwara, Okayama (JP); Ayashi Noguchi, Okayama (JP)

(73) Assignees: Chisso Corporation, Osaka (JP); Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 11/698,910

(22) Filed: Jan. 29, 2007

(65) Prior Publication Data

US 2007/0176544 A1 Aug. 2, 2007

(30) Foreign Application Priority Data

Jan. 31, 2006 (JP) .............................. 2006-022722

(51) Int. Cl.
C07D 405/04 (2006.01)
C07D 311/02 (2006.01)
(52) U.S. Cl. ...................... 546/268.1; 428/917; 549/284
(58) Field of Classification Search ................. 549/284; 428/917; 546/268.1
See application file for complete search history.

(56) References Cited

FOREIGN PATENT DOCUMENTS

| JP | 2004-2285 | 1/2004 |
| JP | 2004-6222 | 1/2004 |
| JP | 2005-32488 | 2/2005 |
| JP | 2005-108720 | 4/2005 |
| JP | 2005-139390 | 6/2005 |
| JP | 2005-247976 | 9/2005 |

OTHER PUBLICATIONS

Manabu Uchida et al., "Structural Optimization of 2,5-Diarylsiloles as Excellent Electron-Transporting Materials for Organic Electroluminescent Devices", Chem. Matter, vol. 13, pp. 2680-2683, 2001.

L.S. Hung et al., "Recent progress of molecular organic electroluminescent materials and devices", Materials Science and Engineering, R. 39, pp. 143-222, 2002.

Manabu Uchida et al., "Relationships between the Structures of Pyridylsilole Derivatives and the Performance for Organic Electroluminescent Device", The 10th International Workshop on Inorganic and Organic Electroluminescence (EL '00), pp. 241-244, 2000.

*Primary Examiner*—Taofiq A Solola
(74) *Attorney, Agent, or Firm*—Wenderoth, Lind & Ponack, L.L.P.

(57) ABSTRACT

Provided are an organic electroluminescent device having better performances in luminous efficiency, device life and driving voltage, a display unit equipped with the same and a lighting instrument equipped with the same. The organic electroluminescent device comprises an electron transport layer containing a specific arylamine-substituted coumarin compound.

27 Claims, 1 Drawing Sheet

COUMARIN COMPOUND, MATERIAL FOR LIGHT EMITTING DEVICE AND ORGANIC ELECTROLUMINESCENT DEVICE

FIELD OF THE INVENTION

The present invention relates to a coumarin compound and a material for a light emitting device containing the same and further to an organic electroluminescent device which is suited as a display device for display units such as color displays. More specifically, it relates to an organic electroluminescent device (hereinafter abbreviated as an organic EL device or merely as device) which is improved in luminous efficiency, life and the like by using a specific compound for an emission layer and an electron transport layer.

BACKGROUND OF THE INVENTION

An organic EL device is a light emitting device of a spontaneous emission type and is expected as a light emitting device for display or lighting, and active researches thereof have been made in recent years. Reduction in driving voltage of the organic EL device and elongation in operation life thereof are indispensable factors for accelerating actual utilization of the device, and they are large problems particularly for blue light emitting devices. Accordingly, organic luminescent materials have been investigated in various manners, and an improvement in styrylallene, anthracene derivatives, coumarin derivatives and the like has been promoted aiming at an improvement in luminous efficiency of the light emitting device and elongation in operation life thereof (for example, Materials Science and Engineering:R: Reports Volume 39, Issues 5 to 6, Pages 143 to 222, 2002 (non-patent document 1), JP H17-139390 A/2005 (patent document 1) and JP H16-6222 A/2004 (patent document 2)). In the above devices, however, Alq3 (tris(8-hydroxyquinoline)aluminum) is used as an electron transport material in many cases, and a large part thereof has high driving voltage and low luminous efficiency.

Then, development of high performance electron transport materials including silole derivatives and phenanthroline derivatives has been promoted, and red light emitting devices and green light emitting devices have been reported, but devices having a markedly long life have not ever been reported in blue light emitting devices (for example, JP H17-32488 A/2005 (patent document 3), JP H17-108720 A/2005 (patent document 4), Proceedings of the 10th International Workshop on Inorganic and Organic Electroluminescence (non-patent document 2) and Chem. Mater. 13, 2680 to 2683, (2001) (non-patent document 3)).

Patent document 1: JP H17-139390 A/2005
Patent document 2: JP H16-6222 A/2004
Patent document 3: JP H17-32488 A/2005
Patent document 4: JP H17-108720 A/2005
Non-patent document 1: Materials Science and Engineering: R: Reports Volume 39, Issues 5 to 6, Pages 143 to 222, 2002
Non-patent document 2: Proceedings of the 10th International Workshop on Inorganic and Organic Electroluminescence
Non-patent document 3: Chem. Mater. 13, 2680 to 2683, (2001).

Under the situation described above, desired are a coumarin compound which is optimally applied to an organic electroluminescent device improved in luminous efficiency, device life, driving voltage and the like in a blue light emitting device and an organic electroluminescent device and a display unit using the same.

SUMMARY OF THE INVENTION

Intensive investigations made by the present inventors in order to solve the problems described above have resulted in finding that an organic electroluminescent device which is improved in luminous efficiency, device life, driving voltage and the like is obtained by using a compound represented by Formula (1) and (1-Z) shown below for an emission layer material and using, in a certain case, a compound represented by Formula (2), (3), (4) (5-1) or (5-2) shown below for an electron transport layer, and thus they have completed the present invention. That is, the present invention provides the following coumarin compound, an organic electroluminescent device comprising the above compound and a display unit and a lighting instrument which are equipped with the above organic electroluminescent device.

[1] A compound represented by the following Formula (1):

(in Formula (1), $\phi$ represents an aromatic group or a heteroaromatic group of an m valence which is constituted by one or plural five-membered rings or six-membered rings and which may be substituted; Z represents a coumarin residue represented by the following Formula (1-Z) which is bonded to $\phi$ described above and which is the same as or different from each other; and m is 2 or more);

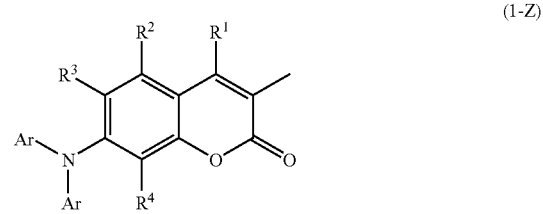

(in Formula (1-Z), $R^1$, $R^2$, $R^3$ and $R^4$ each represent independently hydrogen, alkyl which may be substituted, alkenyl which may be substituted, alkynyl which may be substituted, alkoxy which may be substituted, alkylthio which may be substituted, aryl which may be substituted, aryloxy which may be substituted, arylthio which may be substituted, arylalkyl which may be substituted, arylalkoxy which may be substituted, arylalkylthio which may be substituted, arylalkenyl which may be substituted, arylalkynyl which may be substituted, arylsulfonyloxy which may be substituted, alkylsulfonyloxy which may be substituted, heteroaryl which may be substituted, cycloalkyl which may be substituted, halogen, cyano, nitro or hydroxyl;

Ar each represents independently aryl which may be substituted or heteroaryl which may be substituted; and $R^1$ and $R^2$, $R^2$ and $R^3$, $R^1$ and $R^2$ and $R^3$, or Ar and Ar may be condensed with each other to form a ring(s)).

[2] The compound as described in [1], wherein $\phi$ represents an aromatic group or a heteroaromatic group of an m valence which is constituted by one or plural five-membered rings or six-membered rings and which may be substituted;

m is 2, 3 or 4;

$R^1$, $R^2$, $R^3$ and $R^4$ each represent independently hydrogen, alkyl which may be substituted, alkenyl which may be substituted, alkynyl which may be substituted, aryl which may be substituted, arylalkynyl which may be substituted, heteroaryl which may be substituted, cycloalkyl which may be substituted, halogen or cyano; and Ar each represents independently aryl which may be substituted or heteroaryl which may be substitute.

[3] The compound as described in [1], wherein φ is a benzene ring, a naphthalene ring, an anthracene ring, a phenanthrene ring, a fluorene ring, a terphenyl ring, a biphenyl ring, a pyrene ring, a pyrazine ring, a carbazole ring, a perylene ring or a furan ring each having an m valence, and these rings may be substituted with alkyl having 1 to 4 carbon atoms, phenyl, naphthyl, methylphenyl, ethylphenyl, methylnaphthyl or ethylnaphthyl;

m is 2 or 3;

$R^1$ is hydrogen, alkyl having 1 to 6 carbon atoms, alkenyl having 2 to 6 carbon atoms, alkynyl having 2 to 6 carbon atoms, aryl having 6 to 20 carbon atoms or cyano;

$R^2$, $R^3$ and $R^4$ each represent independently hydrogen or alkyl having 1 to 6 carbon atoms; and Ar is aryl having 6 to 20 carbon atoms, and hydrogen of the above aryl may be substituted with alkyl having 1 to 4 carbon atoms.

[4] The compound as described in [1], wherein φ is a benzene ring, a naphthalene ring, an anthracene ring, a phenanthrene ring, a fluorene ring, a terphenyl ring, a biphenyl ring or a pyrene ring each having an m valence, and these rings may be substituted with alkyl having 1 to 4 carbon atoms;

m is 2 or 3;

$R^1$, $R^2$, $R^3$ and $R^4$ each represent independently hydrogen or alkyl having 1 to 4 carbon atoms; and Ar is phenyl, tolyl, xylyl, biphenylyl, naphthyl, anthracenyl, phenanthryl, terphenylyl, fluorenyl or pyrenyl.

[5] The compound as described in [1], represented by the following Formula (1-1), (1-2), (1-3), (1-4) or (1-5):

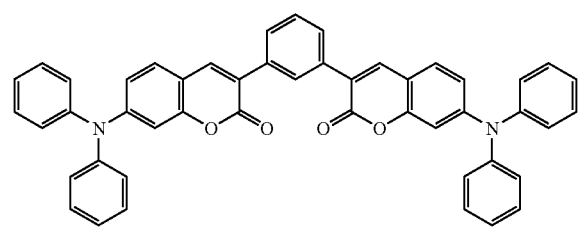

(1-1)

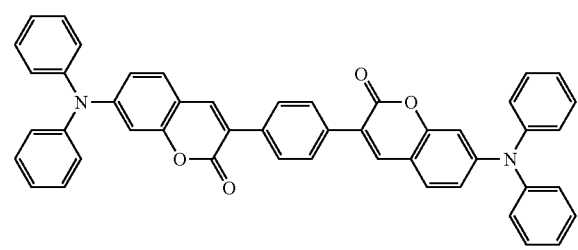

(1-2)

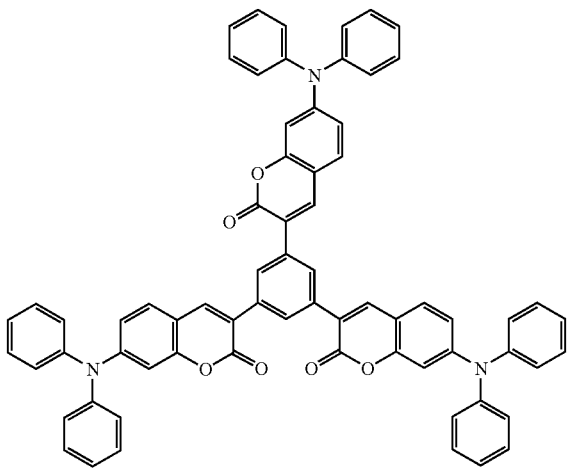

(1-3)

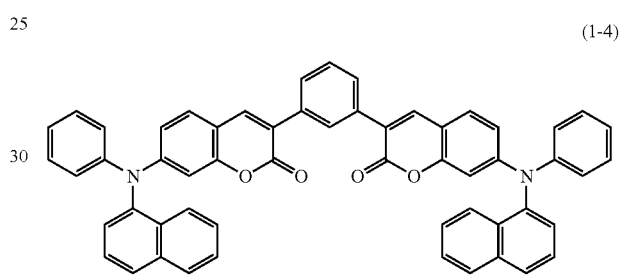

(1-4)

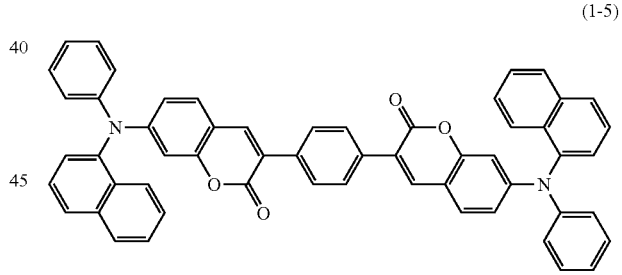

(1-5)

[6] A material for a light emitting device comprising at least one of the compounds as described in any of [1] to [5].

[7] The material for a light emitting device as described in [6], used for an emission layer in the light emitting device.

[8] An organic electroluminescent device comprising a pair of electrodes comprising an anode and a cathode and an emission layer which is disposed between a pair of the above electrodes and which contains at least one of the compounds as described in any of [1] to [5].

[9] The organic electroluminescent device as described in [8], comprising an electron transport layer containing at least one of compounds represented by the following Formula (2) between the cathode and the emission layer each described above:

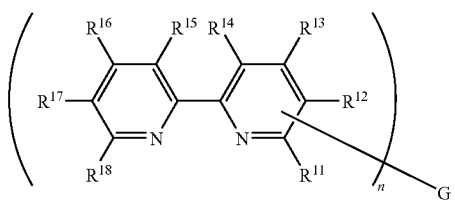

(in Formula (2),

G represents a mere bond or a linkage group of an n valence;

n is 2, 3, 4, 5, 6, 7 or 8;

$R^{11}$, $R^{12}$, $R^{13}$, $R^{14}$, $R^{15}$, $R^{16}$, $R^{17}$ and $R^{18}$ each represent independently hydrogen, alkyl which may be substituted, alkenyl which may be substituted, aryl which may be substituted, arylalkyl which may be substituted, arylalkenyl which may be substituted, boryl which may be substituted, silyl which may be substituted, aralkyl which may be substituted, heteroaryl which may be substituted, cycloalkyl which may be substituted or cyano, and adjacent groups may be combined with each other to form a condensed ring(s);

at least one of $R^{11}$, $R^{12}$, $R^{13}$, $R^{14}$, $R^{15}$, $R^{16}$, $R^{17}$ and $R^{18}$ represents G, and n groups of a 2,2'-bipyridyl residue formed by $R^{11}$, $R^{12}$, $R^{13}$, $R^{14}$, $R^{15}$, $R^{16}$, $R^{17}$ and $R^{18}$ and a 2,2'-bipyridyl nucleus may be the same as or different from each other).

[10] The organic electroluminescent device as described in [9], wherein G represents an aromatic group or a heteroaromatic group of an n valence which is constituted by one or plural five-membered rings or six-membered rings and which may be substituted;

n is 2, 3, 4, 5 or 6;

$R^{11}$, $R^{12}$, $R^{13}$, $R^{14}$, $R^{15}$, $R^{16}$, $R^{17}$ and $R^{18}$ each represent independently hydrogen, alkyl having 1 to 20 carbon atoms which may be substituted, alkenyl having 2 to 20 carbon atoms which may be substituted, aryl having 5 to 30 carbon atoms which may be substituted, arylalkyl having 6 to 30 carbon atoms which may be substituted, arylalkenyl having 6 to 30 carbon atoms which may be substituted, arylboryl, alkylsilyl, aralkyl having 7 to 20 carbon atoms which may be substituted, heteroaryl having 2 to 30 carbon atoms which may be substituted, cycloalkyl having 3 to 10 carbon atoms which may be substituted or cyano; and the substituent in G, $R^{11}$, $R^{12}$, $R^{13}$, $R^{14}$, $R^{15}$, $R^{16}$, $R^{17}$ and $R^{18}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

[11] The organic electroluminescent device as described in [9], wherein G represents an aromatic group or a heteroaromatic group of an n valence which is constituted by one or plural five-membered rings or six-membered rings and which may be substituted, and they may be substituted with alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl;

n is 2, 3 or 4; and $R^{11}$, $R^{12}$, $R^{13}$, $R^{14}$, $R^{15}$, $R^{16}$, $R^{17}$ and $R^{18}$ each represent independently hydrogen, alkyl having 1 to 12 carbon atoms, alkenyl having 2 to 12 carbon atoms, aryl having 5 to 25 carbon atoms, diarylboryl, trialkylsilyl, aralkyl having 7 to 15 carbon atoms, cycloalkyl having 3 to 8 carbon atoms or cyano.

[12] The organic electroluminescent device as described in [9], wherein G represents a benzene ring, a naphthalene ring, an anthracene ring, a phenanthrene ring, a fluorene ring, a terphenyl ring, a biphenyl ring, a thiophene ring, a pyridine ring, a pyrazine ring, a pyrimidine ring, a phenalene ring, a silole ring or a pyridazine ring each having an n valence, and the above rings may be substituted with alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl;

n is 2 or 3; and $R^{11}$, $R^{12}$, $R^{13}$, $R^{14}$, $R^{15}$, $R^{16}$, $R^{17}$ and $R^{18}$ each represent independently hydrogen, alkyl having 1 to 6 carbon atoms, alkenyl having 2 to 6 carbon atoms or aryl having 5 to 20 carbon atoms.

[13] The organic electroluminescent device as described in [9], wherein G represents a benzene ring, a naphthalene ring, an anthracene ring, a phenanthrene ring, a fluorene ring, a thiophene ring, a pyridine ring, a phenalene ring or a silole ring each having an n valence, and the above rings may be substituted with alkyl having 1 to 4 carbon atoms, phenyl, tolyl, xylyl, mesityl, naphthyl, ethylphenyl, methylnaphthyl, ethylnaphthyl or pyridyl;

n is 2 or 3; and $R^{11}$, $R^{12}$, $R^{13}$, $R^{14}$, $R^{15}$, $R^{16}$, $R^{17}$ and $R^{18}$ each represent independently hydrogen, alkyl having 1 to 4 carbon atoms, phenyl, tolyl or xylyl.

[14] The organic electroluminescent device as described in [9], comprising an electron transport layer containing a compound represented by the following Formula (2-1) or Formula (2-2):

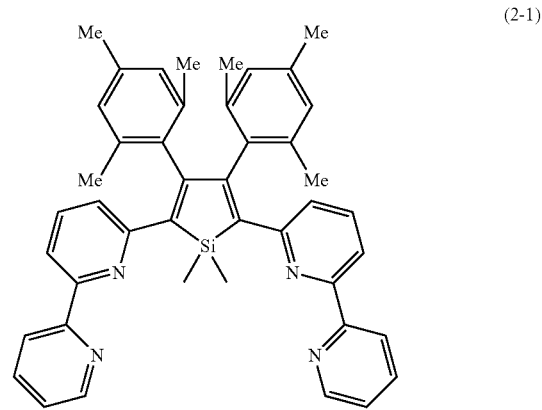

-continued (2-2)

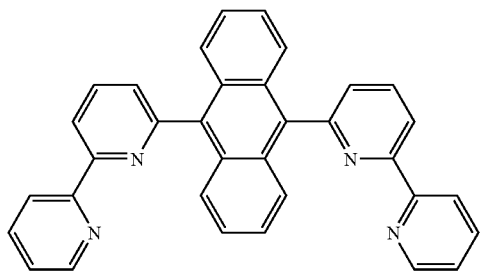

[15] The organic electroluminescent device as described in [8], comprising an electron transport layer containing at least one of compounds represented by the following Formula (3) between the cathode and the emission layer each described above:

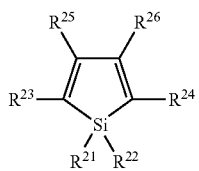

(3)

(in Formula (3),
$R^{21}$, $R^{22}$, $R^{25}$ and $R^{26}$ each represent independently hydrogen, alkyl which may be substituted, alkenyl which may be substituted, aryl which may be substituted, arylalkyl which may be substituted, silyl which may be substituted, aralkyl which may be substituted, heteroaryl which may be substituted, cycloalkyl which may be substituted or cyano; and
$R^{23}$ and $R^{24}$ each represent independently aryl which may be substituted or heteroaryl which may be substituted).

[16] The organic electroluminescent device as described in [15], wherein $R^{21}$, $R^{22}$, $R^{25}$ and $R^{26}$ each represent independently hydrogen, alkyl having 1 to 20 carbon atoms which may be substituted, alkenyl having 2 to 20 carbon atoms which may be substituted, aryl having 5 to 30 carbon atoms which may be substituted, arylalkyl having 6 to 30 carbon atoms which may be substituted, alkylsilyl, aralkyl having 7 to 20 carbon atoms which may be substituted, heteroaryl having 2 to 30 carbon atoms which may be substituted, cycloalkyl having 3 to 10 carbon atoms which may be substituted or cyano;
$R^{23}$ and $R^{24}$ each represent independently heteroaryl having 2 to 30 carbon atoms which may be substituted; and
the substituent in $R^{21}$, $R^{22}$, $R^{23}$, $R^{24}$, $R^{25}$ and $R^{26}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

[17] The organic electroluminescent device as described in [15], wherein $R^{21}$ and $R^{22}$ each represent independently phenyl, naphthyl, alkyl having 1 to 6 carbon atoms or cycloalkyl having 3 to 8 carbon atoms;
$R^{25}$ and $R^{26}$ each represent independently aryl having 5 to 20 carbon atoms which may be substituted or heteroaryl having 2 to 20 carbon atoms which may be substituted;
the substituent in $R^{25}$ and $R^{26}$ is alkyl having 1 to 4 carbon atoms, phenyl, tolyl, xylyl, mesityl, naphthyl, methylnaphthyl, pyridyl or quinolyl;
$R^{23}$ and $R^{24}$ each represent independently heteroaryl having 2 to 20 carbon atoms which may be substituted; and
the substituent in $R^{23}$ and $R^{24}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

[18] The organic electroluminescent device as described in [15], wherein $R^{21}$ and $R^{22}$ each represent independently phenyl, naphthyl, alkyl having 1 to 4 carbon atoms or cycloalkyl having 3 to 6 carbon atoms;
$R^{25}$ and $R^{26}$ each represent independently phenyl, tolyl, xylyl, mesityl, naphthyl, quinolinyl or pyridyl, and they may be substituted with alkyl having 1 to 4 carbon atoms, phenyl, tolyl, xylyl, mesityl, naphthyl, methylnaphthyl, pyridyl or quinolyl;
$R^{23}$ and $R^{24}$ each represent independently phenanthrolinyl, quinolyl, pyridyl, pyrimidinyl, pyrazinyl, pyridazinyl, thienyl, thiazolyl, triazolyl, oxazolyl, oxadiazolyl, imidazolyl, benzoxazolyl, benzothiazolyl, benzothienyl, carbazolyl or thiazolyl, and they may be substituted with phenyl, pyridyl, pyrimidinyl, pyrazinyl, pyridazinyl, imidazolyl, quinolyl, phenanthrolinyl, benzothiazolyl or benzothienyl.

[19] The organic electroluminescent device as described in [8], comprising an electron transport layer containing at least one of compounds represented by the following Formula (4) between the cathode and the emission layer each described above:

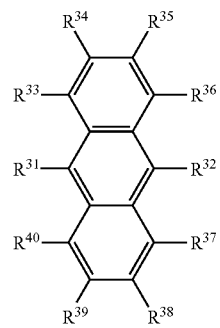

(4)

(in Formula (4),
$R^{31}$ and $R^{32}$ each represent independently heteroaryl which may be substituted;
$R^{33}$, $R^{34}$, $R^{35}$, $R^{36}$, $R^{37}$, $R^{38}$, $R^{39}$ and $R^{40}$ each represent independently hydrogen, alkyl which may be substituted, aryl which may be substituted, boryl which may be substituted, silyl which may be substituted, aralkyl which may be substituted, heteroaryl which may be substituted, cycloalkyl which may be substituted or cyano, and adjacent groups may be combined with each other to form a condensed ring(s)).

[20] The organic electroluminescent device as described in [19], wherein $R^{31}$ and $R^{32}$ each represent independently heteroaryl having 2 to 30 carbon atoms which may be substituted;
$R^{33}$, $R^{34}$, $R^{35}$, $R^{36}$, $R^{37}$, $R^{38}$, $R^{39}$ and $R^{40}$ each represent independently hydrogen, alkyl having 1 to 20 carbon atoms which may be substituted, aryl having 5 to 30 carbon atoms which may be substituted, arylboryl, alkylsilyl, aralkyl having 7 to 20 carbon atoms which may be substituted, heteroaryl having 2 to 30 carbon atoms which may be substituted, cycloalkyl having 3 to 10 carbon atoms which may be substituted or cyano; and the substituent in $R^{31}$, $R^{32}$, $R^{33}$, $R^{34}$, $R^{35}$, $R^{36}$, $R^{37}$, $R^{38}$, $R^{39}$ and $R^{40}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

[21] The organic electroluminescent device as described in [19], wherein $R^{31}$ and $R^{32}$ each represent independently heteroaryl having 2 to 25 carbon atoms which may be substituted;

the substituent in $R^{31}$ and $R^{32}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl; and $R^{33}$, $R^{34}$, $R^{35}$, $R^{36}$, $R^{37}$, $R^{38}$, $R^{39}$ and $R^{40}$ each represent independently hydrogen, alkyl having 1 to 12 carbon atoms, aryl having 5 to 25 carbon atoms, diarylboryl, trialkylsilyl, aralkyl having 7 to 15 carbon atoms, cycloalkyl having 3 to 8 carbon atoms or cyano.

[22] The organic electroluminescent device as described in [19], wherein $R^{31}$ and $R^{32}$ each represent independently pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl, and they may be substituted with pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl; and $R^{33}$, $R^{34}$, $R^{35}$, $R^{36}$, $R^{37}$, $R^{38}$, $R^{39}$ and $R^{40}$ each represent independently hydrogen, alkyl having 1 to 4 carbon atoms, phenyl, tolyl or xylyl.

[23] The organic electroluminescent device as described in [8], comprising an electron transport layer containing at least one of compounds represented by the following Formula (5-1) or (5-2) between the cathode and the emission layer each described above:

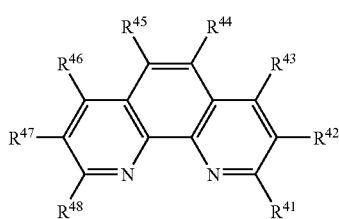

(5-1)

(in Formula (5-1), $R^{41}$, $R^{42}$, $R^{43}$, $R^{44}$, $R^{45}$, $R^{46}$, $R^{47}$ and $R^{48}$ each represent independently hydrogen, alkyl which may be substituted, alkenyl which may be substituted, aryl which may be substituted, arylalkyl which may be substituted, boryl which may be substituted, silyl which may be substituted, aralkyl which may be substituted, heteroaryl which may be substituted, cycloalkyl which may be substituted or cyano, and adjacent groups may be combined with each other to form a condensed ring(s));

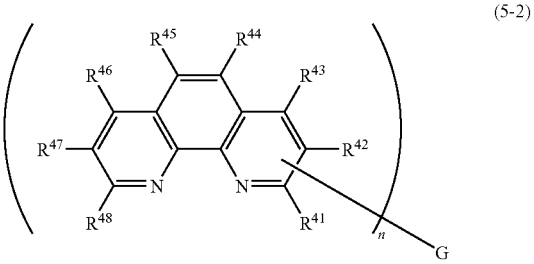

(5-2)

(in Formula (5-2), G represents a mere bond or a linkage group of an n valence;

n is 2, 3, 4, 5, 6, 7 or 8;

$R^{41}$, $R^{42}$, $R^{43}$, $R^{44}$, $R^{45}$, $R^{46}$, $R^{47}$ and $R^{48}$ each represent independently hydrogen, alkyl which may be substituted, alkenyl which may be substituted, aryl which may be substituted, arylalkyl which may be substituted, boryl which may be substituted, silyl which may be substituted, aralkyl which may be substituted, heteroaryl which may be substituted, cycloalkyl which may be substituted or cyano, and adjacent groups may be combined with each other to form a condensed ring(s);

at least one of $R^{41}$, $R^{42}$, $R^{43}$, $R^{44}$, $R^{45}$, $R^{46}$, $R^{47}$ and $R^{48}$ represents G, and n groups of a phenanthroline residue formed by $R^{41}$, $R^{42}$, $R^{43}$, $R^{44}$, $R^{45}$, $R^{46}$, $R^{47}$ and $R^{48}$ and a phenanthroline nucleus may be the same as or different from each other).

[24] The organic electroluminescent device as described in [23], wherein G represents an aromatic group or a heteroaromatic group of an n valence which is constituted by one or plural five-membered rings or six-membered rings and which may be substituted;

n is 2, 3, 4, 5 or 6;

$R^{41}$, $R^{42}$, $R^{43}$, $R^{44}$, $R^{45}$, $R^{46}$, $R^{47}$ and $R^{48}$ each represent independently hydrogen, alkyl having 1 to 20 carbon atoms which may be substituted, alkenyl having 2 to 20 carbon atoms which may be substituted, aryl having 5 to 30 carbon atoms which may be substituted, arylalkyl having 6 to 30 carbon atoms which may be substituted, arylboryl, alkylsilyl, aralkyl having 7 to 20 carbon atoms which may be substituted, heteroaryl having 2 to 30 carbon atoms which may be substituted, cycloalkyl having 3 to 10 carbon atoms which may be substituted or cyano; and the substituent in G, $R^{41}$, $R^{42}$, $R^{43}$, $R^{44}$, $R^{45}$, $R^{46}$, $R^{47}$ and $R^{48}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

[25] The organic electroluminescent device as described in [23], wherein G represents an aromatic group or a heteroaromatic group of an n valence which is constituted by one or plural five-membered rings or six-membered rings and which may be substituted, and they may be substituted with alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl;

n is 2, 3 or 4; and $R^{41}$, $R^{42}$, $R^{43}$, $R^{44}$, $R^{45}$, $R^{46}$, $R^{47}$ and $R^{48}$ each represent independently hydrogen, alkyl having 1 to 12 carbon atoms, alkenyl having 2 to 12 carbon atoms, aryl having 5 to 25 carbon atoms, diarylboryl, trialkylsilyl, aralkyl having 7 to 15 carbon atoms, cycloalkyl having 3 to 8 carbon atoms or cyano.

[26] The organic electroluminescent device as described in [23], wherein G represents a benzene ring, a naphthalene ring, an anthracene ring, a phenanthrene ring, a fluorene ring, a terphenyl ring, a biphenyl ring, a thiophene ring, a pyridine ring, a pyrazine ring, a pyrimidine ring, a phenalene ring, a silole ring or a pyridazine ring each having an n valence, and the above rings may be substituted with alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl;

n is 2 or 3; and $R^{41}$, $R^{42}$, $R^{43}$, $R^{44}$, $R^{45}$, $R^{46}$, $R^{47}$ and $R^{48}$ each represent independently hydrogen, alkyl having 1 to 6 carbon atoms, alkenyl having 2 to 6 carbon atoms or aryl having 5 to 20 carbon atoms.

[27] The organic electroluminescent device as described in [23], wherein G represents a benzene ring, a naphthalene ring, an anthracene ring, a phenanthrene ring, a fluorene ring, a thiophene ring, a pyridine ring, a phenalene ring or a silole ring each having an n valence, and the above rings may be substituted with alkyl having 1 to 4 carbon atoms, phenyl, tolyl, xylyl, mesityl, naphthyl, ethylphenyl, methylnaphthyl, ethylnaphthyl or pyridyl;

n is 2 or 3; and $R^{41}$, $R^{42}$, $R^{43}$, $R^{44}$, $R^{45}$, $R^{46}$, $R^{47}$ and $R^{48}$ each represent independently hydrogen, alkyl having 1 to 4 carbon atoms, phenyl, tolyl or xylyl.

[28] The organic electroluminescent device as described in [23], comprising an electron transport layer containing a compound represented by the following Formula (5-1-1):

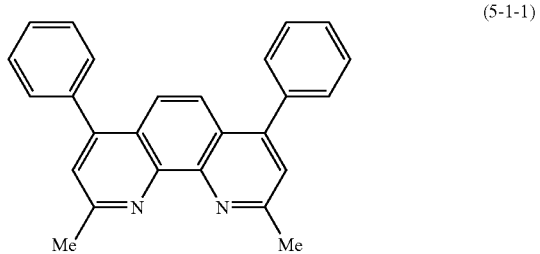

(5-1-1)

[29] A display unit comprising the organic electroluminescent device as described in any of [8] to [28].

[30] A lighting instrument comprising the organic electroluminescent device as described in any of [8] to [28].

According to the preferred embodiment of the present invention, an organic electroluminescent device which has high luminous efficiency and elongated device life and which is reduced in driving voltage can be provided. In particular, conventional problems on a blue and fluorescent light emitting device such as high driving voltage and short device life can be solved. Further, a display unit, a lighting instrument and the like which are equipped with the above effective organic electroluminescent device can be provided as well.

EXPLANATIONS OF CODES

Figure 1:
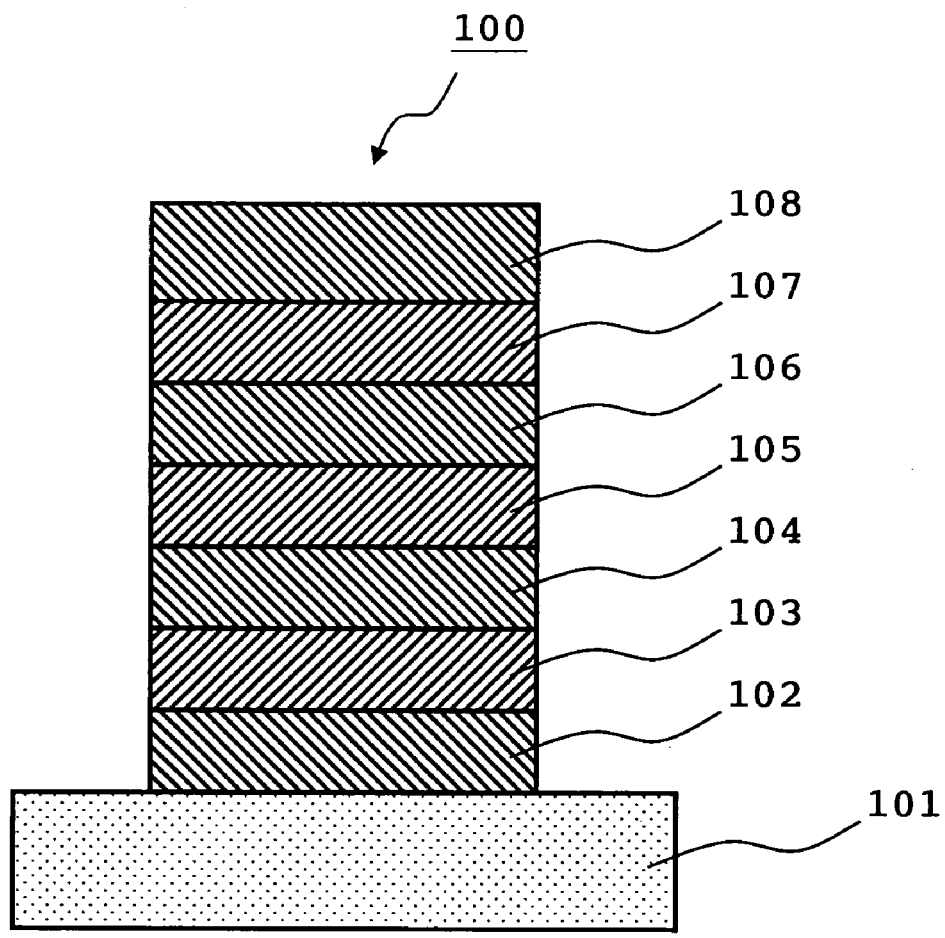
FIG. 1 is an outline cross-sectional drawing showing the organic electroluminescent device according to the present embodiment.

100 Organic electroluminescent device
101 Substrate
102 Anode
103 Hole injection layer
104 Hole transport layer
105 Emission layer
106 Electron transport layer
107 Electron injection layer
108 Cathode

DETAILED DESCRIPTION OF THE INVENTION

1. Explanation of the Compound of the Present Invention Represented by Formula (1)

The compound of the present invention is a compound represented by Formula (1) described above. The compound represented by Formula (1) described above shall be explained below.

φ in Formula (1) represents an aromatic group or a heteroaromatic group of an m valence which is constituted by one or plural five-membered rings or six-membered rings and which may be substituted. The aromatic group or heteroaromatic group of an m valence means a residue obtained by removing m atoms of a hydrogen atom or a substituent from an optional aromatic hydrocarbon compound or aromatic heterocyclic hydrocarbon compound and a combination thereof, and to be specific, it means a linkage group of an m valence which is an aromatic ring having m pieces of a bond.

The aromatic ring includes, for example, a benzene ring, a naphthalene ring, an anthracene ring, a fluorene ring, a biphenyl ring, a terphenyl ring, an azulene ring, a phenanthrene ring, a triphenylene ring, a pyrene ring, a crysene ring, a naphthacene ring, a perylene ring, a pentacene ring, a hexacene ring, a coronene ring, a trinaphthylene ring, a furan ring, a thiophene ring, a pyrrole ring, an imidazole ring, a pyrazole ring, a 1,2,4-triazole ring, a 1,2,3-triazole ring, an oxazole ring, a thiazole ring, an isooxazole ring, an isothiazole ring, a furazan ring, a pyridine ring, a pyrazine ring, a pyrimidine ring, a pyridazine ring, an indolizine ring, a quinoline ring, an isoindole ring, an indole ring, an isoquinoline ring, a phthalazine ring, a purine ring, a naphthyridine ring, a quinoxaline ring, a quinazoline ring, a cinnoline ring, a pteridine ring, a carbazole ring, a phenanthridine ring, an acridine ring, a perimidine ring, a phenanthroline ring and a phenazine ring. They each may have independently plural optional substituents, and the plural substituents may be condensed with each other to further form a ring(s).

It is more preferably a benzene ring, a naphthalene ring, an anthracene ring, a phenanthrene ring, a fluorene ring, a terphenyl ring, a biphenyl ring, a pyrene ring, a pyrazine ring, a carbazole ring, a perylene ring or a furan ring, and these rings may be substituted. It is further preferably a benzene ring, a naphthalene ring, an anthracene ring, a phenanthrene ring, a fluorene ring, a terphenyl ring, a biphenyl ring or a pyrene ring, and these rings may be substituted.

The "substituent" in "each may have independently plural optional substituents" includes, for example, aliphatic hydrocarbon groups such as methyl, ethyl, propyl, isopropyl, s-butyl, t-butyl and pentyl, alicyclic hydrocarbon groups such as cyclopropyl, cyclobutyl, cyclopentyl, cyclohexyl and cycloheptyl, aromatic hydrocarbon groups such as phenyl, o-tolyl, m-tolyl, xylyl, mesityl, o-cumenyl, m-cumenyl, p-cumenyl, naphthyl, anthracenyl, phenanthryl, biphenylyl, methylphenyl, ethylphenyl, butyiphenyl, methylnaphthyl, dimethylnaphthyl, ethylnaphthyl, diethylnaphthyl and butylnaphthyl, heterocyclic groups such as pyridyl, quinazolyl, quinolyl, pyrimidinyl, furyl, thienyl, pyrrolyl, imidazolyl, tetrazolyl and phenanthrolinyl, alkoxyl groups such as methoxy, ethoxy, propoxy, phenoxy and benzyloxy, and the like.

More preferred "substituent" is alkyl having 1 to 4 carbon atoms, phenyl, naphthyl, methylphenyl, ethylphenyl, methylnaphthyl or ethylnaphthyl. Further preferred "substituent" is alkyl having 1 to 4 carbon atoms.

φ in Formula (1) includes, to be specific, the following aromatic groups, heteroaromatic groups or the like of an m valence.

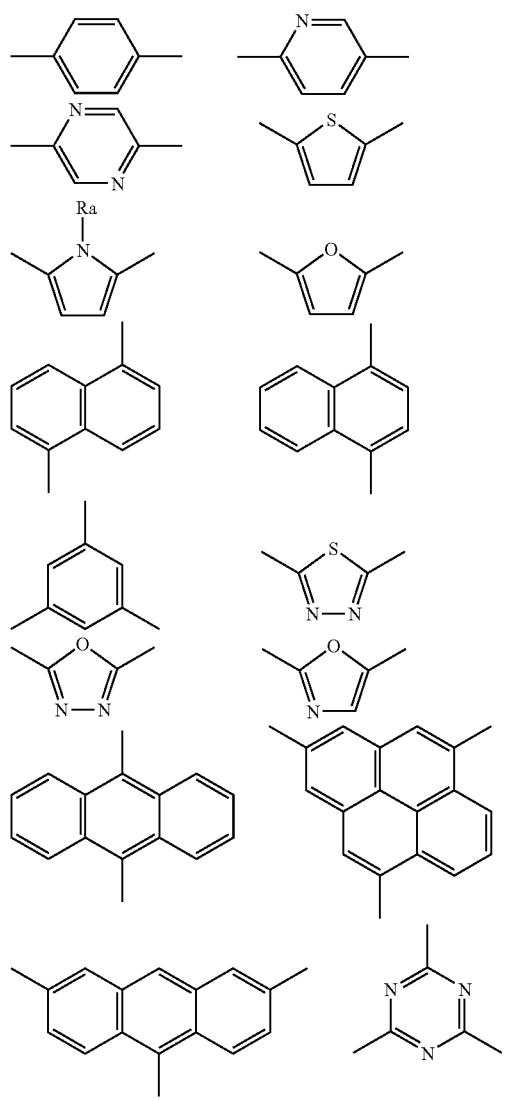

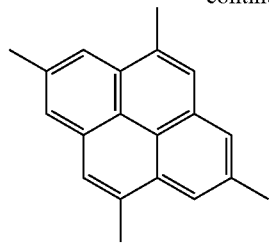

φ in Formula (1) can be obtained by combining plural aromatic rings described above and includes a group having the following formula:

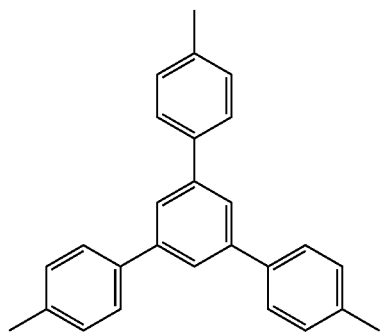

The number m in Formula (1) includes an integer of 2 or more, preferably 2 to 4, more preferably 2 or 3 and further preferably 2.

"Alkyl" in "alkyl which may be substituted" in $R^1$ to $R^4$ of Formula (1-Z) may be either a linear or branched chain and includes, for example, linear alkyl having 1 to 20 carbon atoms or branched alkyl having 3 to 20 carbon atoms. Preferred "alkyl" is alkyl having 1 to 12 carbon atoms (branched alkyl having 3 to 12 carbon atoms). More preferred "alkyl" is alkyl having 1 to 6 carbon atoms (branched alkyl having 3 to 6 carbon atoms). Particularly preferred "alkyl" is alkyl having 1 to 4 carbon atoms (branched alkyl having 3 to 4 carbon atoms). Specific "alkyl" includes methyl, ethyl, propyl, isopropyl, butyl, isobutyl, s-butyl, t-butyl, pentyl, hexyl, heptyl, octyl and the like.

"Alkenyl" in "alkenyl which may be substituted" in $R^1$ to $R^4$ of Formula (1-Z) may be either a linear or branched chain and includes, for example, linear or branched alkenyl having 2 to 20 carbon atoms. Preferred "alkenyl" is alkenyl having 2 to 12 carbon atoms. More preferred "alkenyl" is alkenyl having 2 to 6 carbon atoms. Particularly preferred "alkenyl" is alkenyl having 2 to 4 carbon atoms. To be specific, it includes vinyl, propenyl, isopropenyl, allyl, butenyl, pentenyl, geranyl, farnesyl and the like.

"Alkynyl" in "alkynyl which may be substituted" in $R^1$ to $R^4$ of Formula (1-Z) may be either a linear or branched chain and includes, for example, linear or branched alkynyl having 2 to 20 carbon atoms. Preferred "alkynyl" is alkynyl having 2 to 12 carbon atoms. More preferred "alkynyl" is alkynyl having 2 to 6 carbon atoms. Particularly preferred "alkynyl" is alkynyl having 2 to 4 carbon atoms. To be specific, it includes ethynyl, propynyl, butynyl and the like.

"Alkoxy" in "alkoxy which may be substituted" in $R^1$ to $R^4$ of Formula (1-Z) includes, for example, alkoxy having 1 to 20 carbon atoms. Preferred "alkoxy" is alkoxy having 1 to 15 carbon atoms. More preferred "alkoxy" is alkoxy having 1 to 10 carbon atoms. Specific "alkoxy" includes methoxy, ethoxy, propoxy, isopropoxy, butoxy, isobutoxy, s-butoxy, t-butoxy, pentyloxy, cyclopentyloxy, hexyloxy, cyclohexyloxy, heptyloxy, cycloheptyloxy, octyloxy, cyclooctyloxy, phenoxy and the like.

"Alkylthio" in "alkylthio which may be substituted" in $R^1$ to $R^4$ of Formula (1-Z) includes alkylthio having 1 to 20 carbon atoms. Preferred "alkylthio" is alkylthio having 1 to 15 carbon atoms. More preferred "alkylthio" is alkylthio having 1 to 10 carbon atoms. Specific "alkylthio" includes methylthio, ethylthio, propylthio, isopropylthio, butylthio, isobutylthio, s-butylthio, t-butylthio, pentylthio, cyclopentylthio, hexylthio, cyclohexylthio, heptylthio, cycloheptylthio, octylthio, cyclooctylthio and the like.

"Aryl" in "aryl which may be substituted" in $R^1$ to $R^4$ of Formula (1-Z) includes, for example, aryl having 5 to 30 carbon atoms. Preferred "aryl" is aryl having 5 to 25 carbon atoms. More preferred "aryl" is aryl having 6 to 20 carbon atoms. Specific "aryl" includes phenyl, tolyl, xylyl, mesityl, biphenylyl, naphthyl, anthracenyl, phenanthryl, terphenylyl, fluorenyl, pyrenyl and the like. Particularly preferred "aryl" is phenyl, tolyl, xylyl, mesityl or naphthyl.

"Aryloxy" in "aryloxy which may be substituted" in $R^1$ to $R^4$ of Formula (1-Z) includes aryloxy having 6 to 20 carbon atoms. Preferred "aryloxy" is aryloxy having 6 to 16 carbon atoms. More preferred "aryloxy" is aryloxy having 6 to 13 carbon atoms. Specific "aryloxy" includes phenyloxy, naphthyloxy, anthracenyloxy, phenanthryloxy and the like. "Aryl" in "aryloxy" includes the aryls described above.

"Arylthio" in "arylthio which may be substituted" in $R^1$ to $R^4$ of Formula (1-Z) includes arylthio having 6 to 30 carbon atoms. Preferred "arylthio" is arylthio having 6 to 25 carbon atoms. More preferred "arylthio" is arylthio having 6 to 20 carbon atoms. Specific "arylthio" includes phenylthio, naphthylthio, anthracenylthio, phenanthrylthio and the like. "Aryl" in "arylthio" includes the aryls described above.

"Arylalkyl" in "arylalkyl which may be substituted" in $R^1$ to $R^4$ of Formula (1-Z) includes arylalkyl having 6 to 30 carbon atoms. Preferred "arylalkyl" is arylalkyl having 6 to 25 carbon atoms. More preferred "arylalkyl" is arylalkyl having 6 to 20 carbon atoms. Specific "arylalkyl" includes arylmethyl, arylethyl and the like. "Aryl" in "arylalkyl" includes the aryls described above. "Alkyl" in "arylalkyl" includes the alkyls described above and cycloalkyls described later.

"Arylalkoxy" in "arylalkoxy which may be substituted" in $R^1$ to $R^4$ of Formula (1-Z) includes arylalkoxy having 6 to 30 carbon atoms. Preferred "arylalkoxy" is arylalkoxy having 6 to 25 carbon atoms. More preferred "arylalkoxy" is arylalkoxy having 6 to 20 carbon atoms. Specific "arylalkoxy" includes arylmethoxy, arylethoxy and the like. "Aryl" in "arylalkoxy" includes the aryls described above. "Alkoxy" in "arylalkoxy" includes the alkoxys described above.

"Arylalkylthio" in "arylalkylthio which may be substituted" in $R^1$ to $R^4$ of Formula (1-Z) includes arylalkylthio having 6 to 30 carbon atoms. Preferred "arylalkylthio" is arylalkylthio having 6 to 25 carbon atoms. More preferred "arylalkylthio" is arylalkylthio having 6 to 20 carbon atoms. Specific "arylalkylthio" includes arylmethylthio, arylethylthio and the like. "Aryl" in "arylalkylthio" includes the aryls described above. "Alkylthio" in "arylalkylthio" includes the alkylthios described above.

"Arylalkenyl" in "arylalkenyl which may be substituted" in $R^1$ to $R^4$ of Formula (1-Z) includes arylalkenyl having 6 to 30 carbon atoms. Preferred "arylalkenyl" is arylalkenyl having 6 to 25 carbon atoms. More preferred "arylalkenyl" is arylalkenyl having 6 to 20 carbon atoms. Specific "arylalkenyl" includes arylvinyl, arylpropenyl, arylisopropenyl and the like. "Aryl" in "arylalkenyl" includes the aryls described above. "Alkenyl" in "arylalkenyl" includes the alkenyls described above.

"Arylalkynyl" in "arylalkynyl which may be substituted" in $R^1$ to $R^4$ of Formula (1-Z) includes arylalkynyl having 6 to 30 carbon atoms. Preferred "arylalkynyl" is arylalkynyl having 6 to 25 carbon atoms. More preferred "arylalkynyl" is arylalkynyl having 6 to 20 carbon atoms. Specific "arylalkynyl" includes arylethynyl, arylpropynyl and the like. "Aryl" in "arylalkynyl" includes the aryls described above. "Alkynyl" in "arylalkynyl" includes the alkynyls described above.

"Arylsulfonyloxy which may be substituted" in $R^1$ to $R^4$ of Formula (1-Z) includes benzenesulfonyloxy, p-toluenesulfonyloxy, mesitylenesulfonyloxy, naphthalenesulfonyloxy and the like.

"Alkylsulfonyloxy which may be substituted" in $R^1$ to $R^4$ of Formula (1-Z) includes methanesulfonyloxy, ethanesulfonyloxy, butanesulfonyloxy, octanesulfonyloxy, trifluoromethanesulfonyloxy and the like.

"Heteroaryl" in "heteroaryl which may be substituted" in $R^1$ to $R^4$ of Formula (1-Z) includes, for example, a heterocyclic group containing 1 to 5 hetero atoms selected from oxygen atoms, sulfur atoms and nitrogen atoms other than carbon atoms as ring constituting atoms. Paying attentions to a carbon atom which is the constituting atom other than the hetero atoms, it includes, for example, heteroaryl having 2 to 30 carbon atoms, preferably heteroaryl having 2 to 25 carbon atoms and more preferably heteroaryl having 2 to 20 carbon atoms. It includes, for example, furyl, thienyl, pyrrolyl, oxazolyl, isooxazolyl, thiazolyl, isothiazolyl, imidazolyl, pyrazolyl, oxadiazolyl, frazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathienyl, thianthrenyl, indolidinyl and phenanthrolinyl, and preferred are, for example, thienyl, pyrazinyl, benzothiazolyl, benzo[b]thienyl and carbazolyl.

"Cycloalkyl" in "cycloalkyl which may be substituted" in $R^1$ to $R^4$ of Formula (1-Z) includes, for example, cycloalkyl having 3 to 10 carbon atoms. Preferred "cycloalkyl" is cycloalkyl having 3 to 8 carbon atoms. More preferred "cycloalkyl" is a cycloalkyl having 3 to 6 carbon atoms. Specific "cycloalkyl" includes cyclopropyl, cyclobutyl, cyclopentyl, methylcyclopentyl, cyclohexyl, methylcyclohexyl, dimethylcyclohexyl, cycloheptyl, cyclooctyl or the like.

"Halogen" in $R^1$ to $R^4$ of Formula (1-Z) includes F, Cl, Br, I and the like.

The "substituents" in $R^1$ to $R^4$ of Formula (1-Z) include, for example, alkyl such as methyl, ethyl, propyl, isopropyl, butyl, isobutyl, s-butyl, t-butyl, pentyl, cyclopentyl, hexyl, cyclohexyl, heptyl, cycloheptyl, octyl, cyclooctyl and trifluoromethyl; aryl such as phenyl, tolyl, xylyl, mesityl, naphthyl, anthracenyl and phenanthryl; alkylaryl such as methylphenyl, ethylphenyl, s-butylphenyl, t-butylphenyl, 1-methylnaphthyl, 2-methylnaphthyl, 4-methylnaphthyl, 1,6-dimethylnaphthyl, 1-ethylnaphthyl, 2-ethylnaphthyl, 4-ethylnaphthyl, 1,6-diethylnaphthyl and 4-t-butylnaphthyl; heterocycle such as pyridyl, quinazolinyl, quinolyl, pyrimidinyl, pyrazinyl, pyridazinyl, furyl, thienyl, pyrrolyl, imidazolyl, tetrazolyl, thiazolyl, triazolyl, oxazolyl, oxadiazolyl, benzoxazolyl, benzothiazolyl, benzothienyl, carbazolyl and phenanthrolinyl; cyano; and the like. The number of the substituent is, for example, a maximum substitutable number, and it is preferably 0 to 3, more preferably 0 to 2.

Aryl which may be substituted or heteroaryl which may be substituted in Ar of Formula (1-Z) include the same ones as those described in explanations of $R^1$ to $R^4$ in Formula (1-Z), and the same ones are preferred.

The compound represented by Formula (1-1), (1-2), (1-3), (1-4) or (1-5) described above can be given as further specific examples of the compound represented by Formula (1) described above. Further, compounds represented by Formula (1-6) to (1-26) shown below can be given as well.

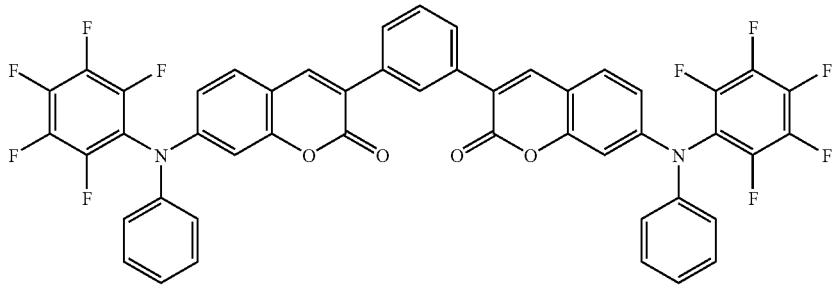

(1-6)

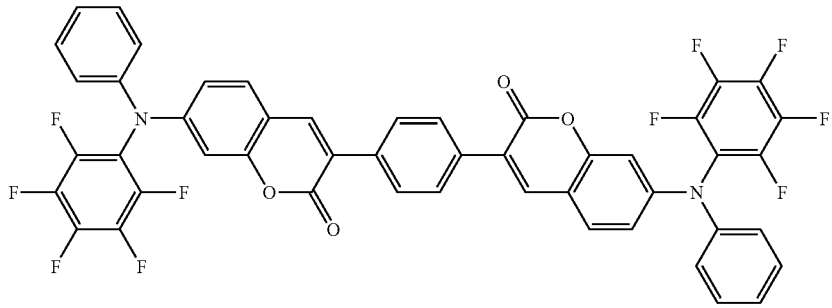

(1-7)

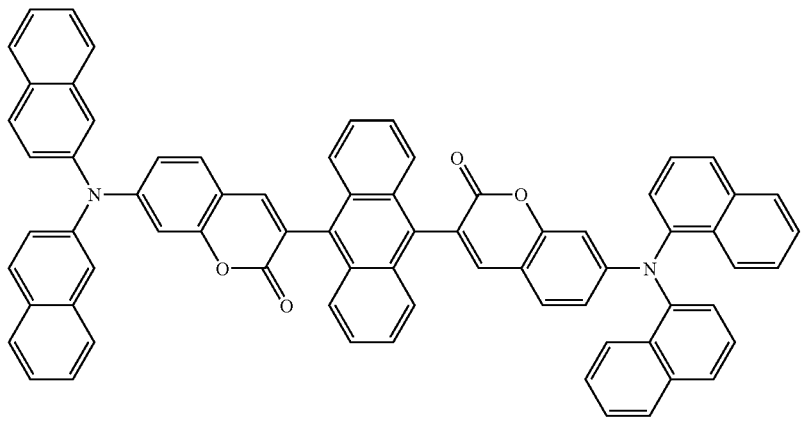

(1-8)

(1-9)
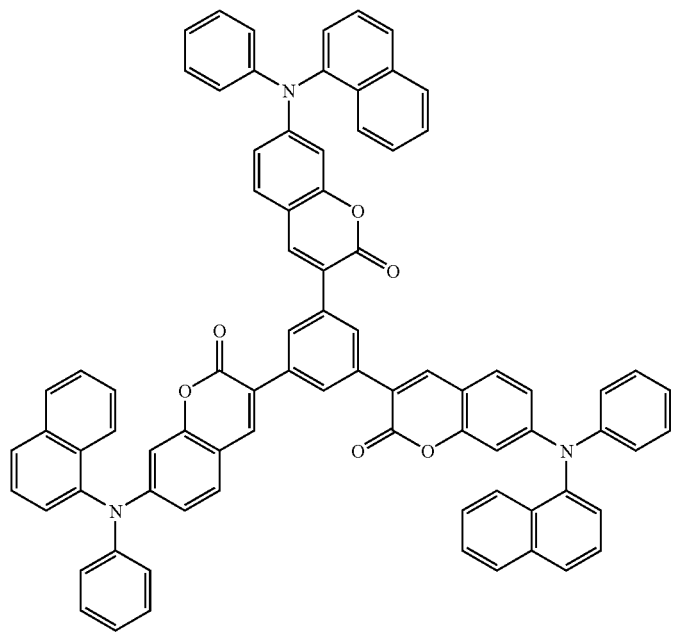
(1-10)
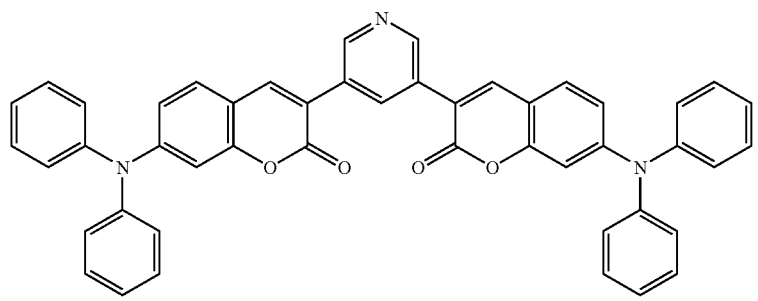
(1-11)
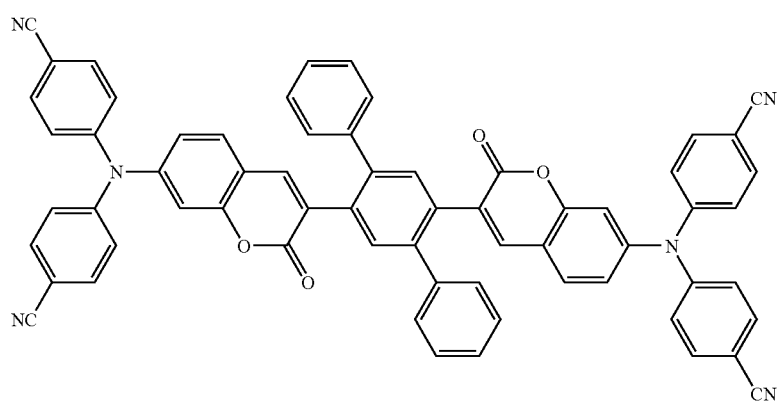

-continued
(1-12)
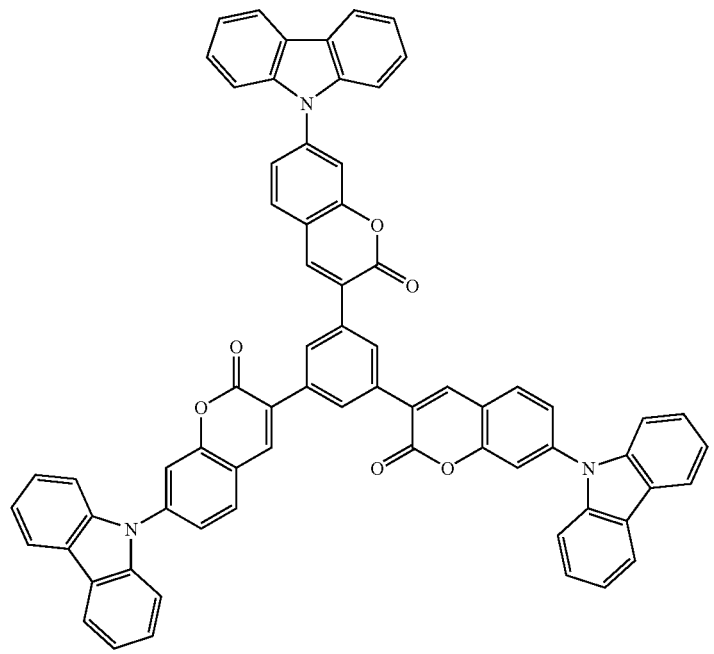
(1-13)
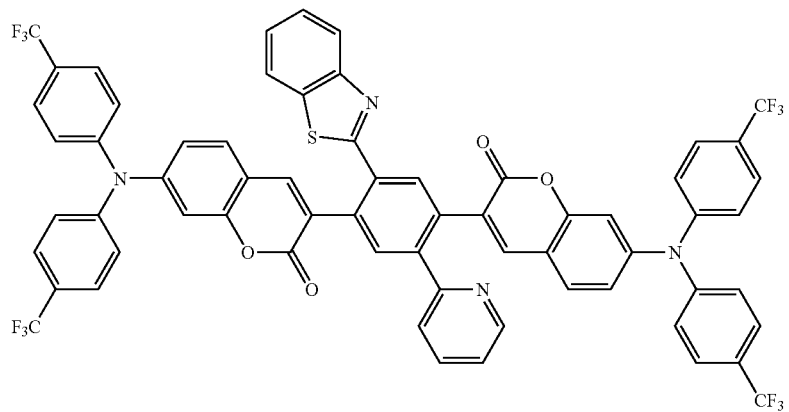
(1-14)
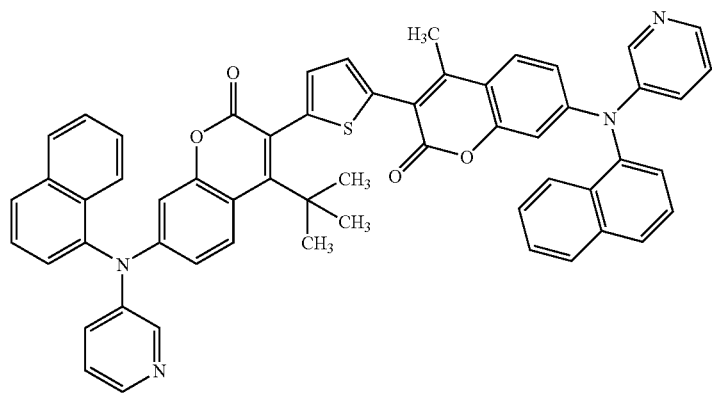

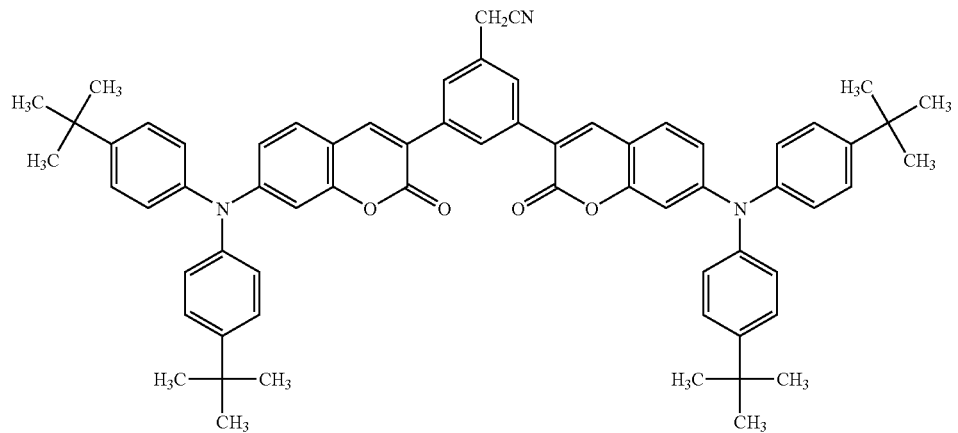
(1-15)
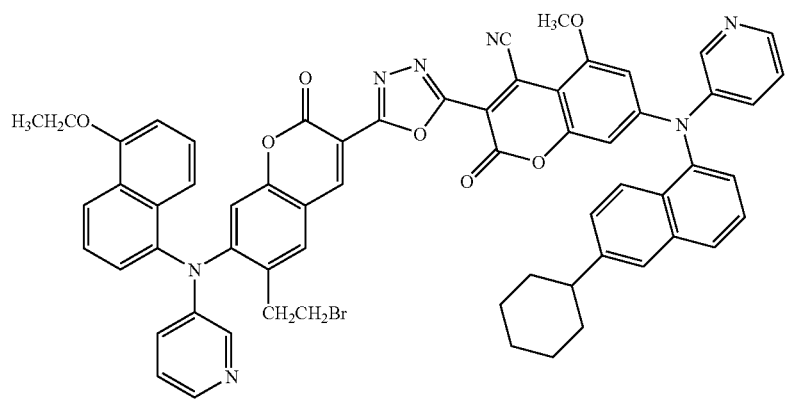
(1-16)
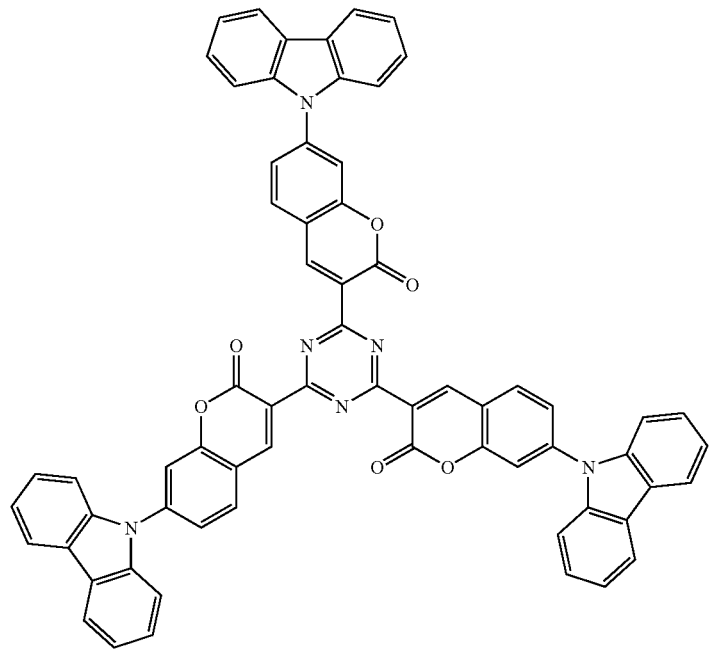
(1-17)

-continued
(1-18)
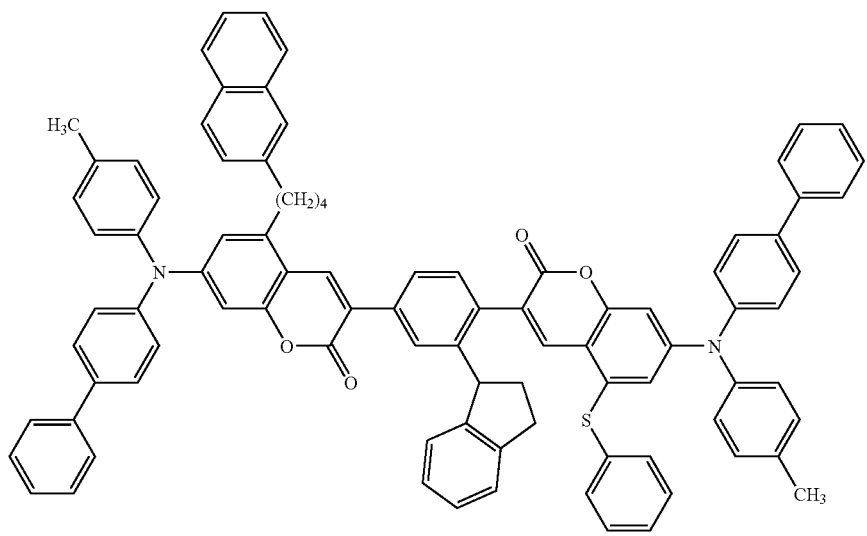
(1-19)
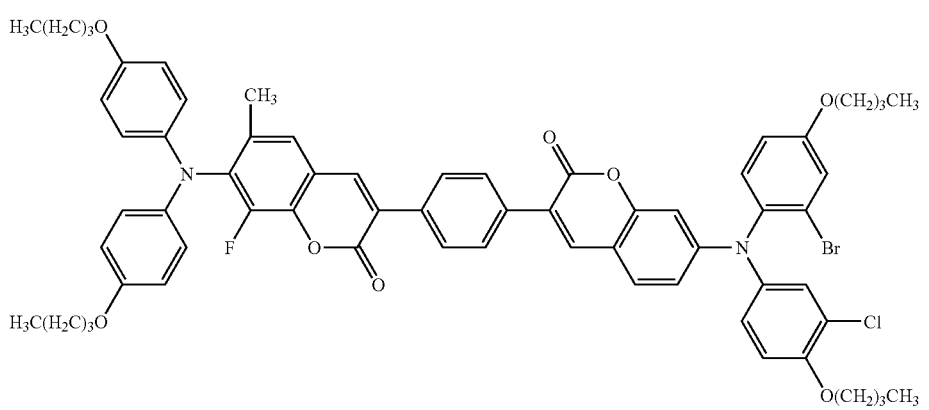
(1-20)
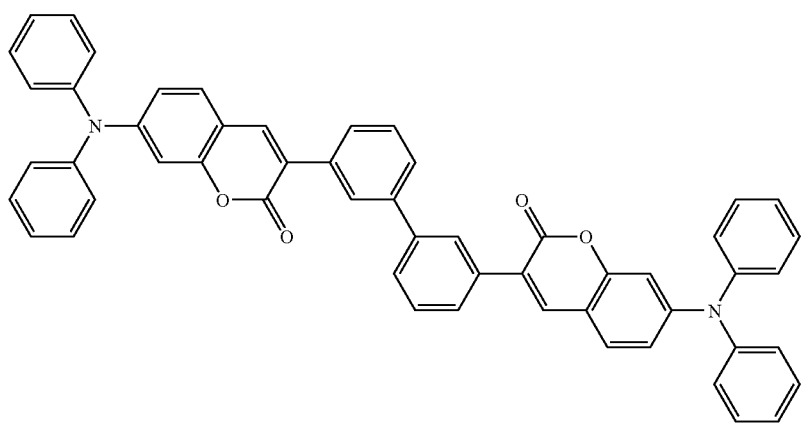

-continued
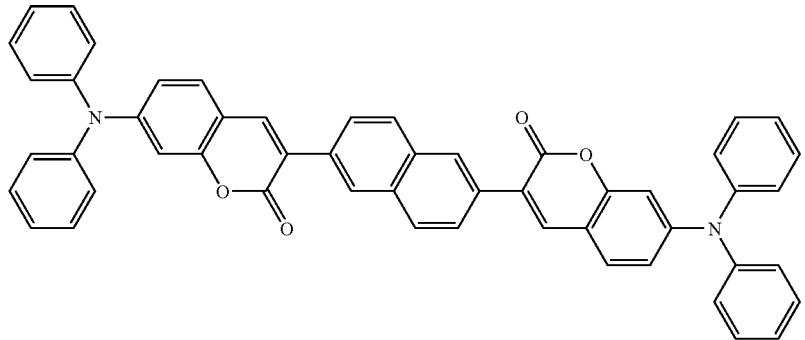
(1-21)
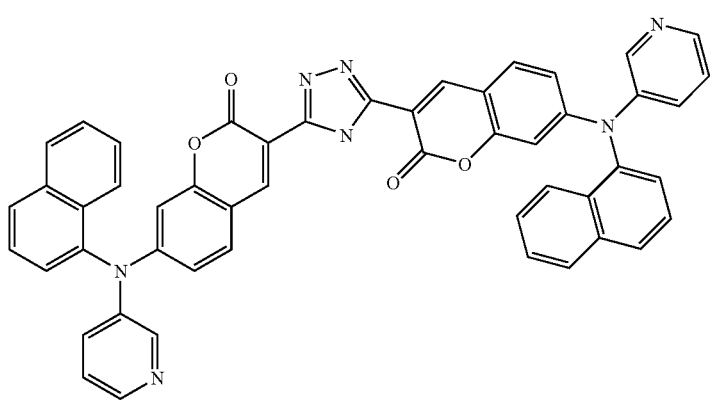
(1-22)
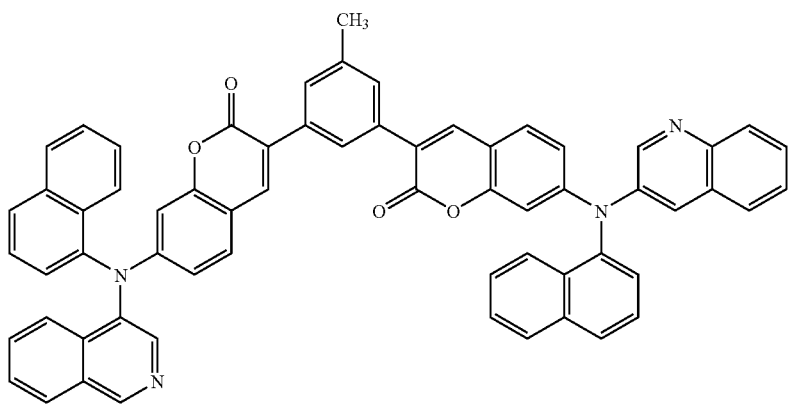
(1-23)
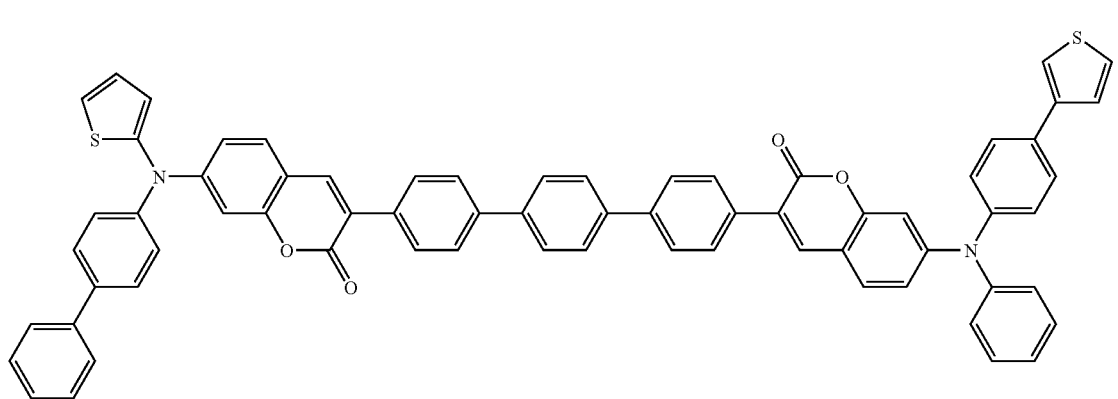
(1-24)

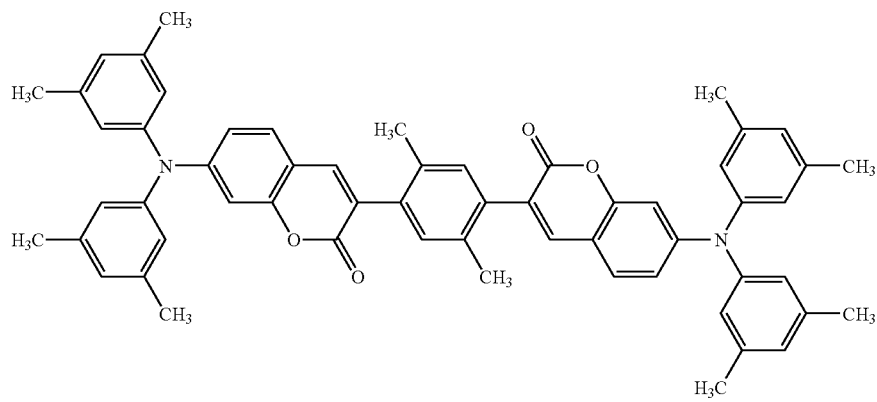
(1-25)

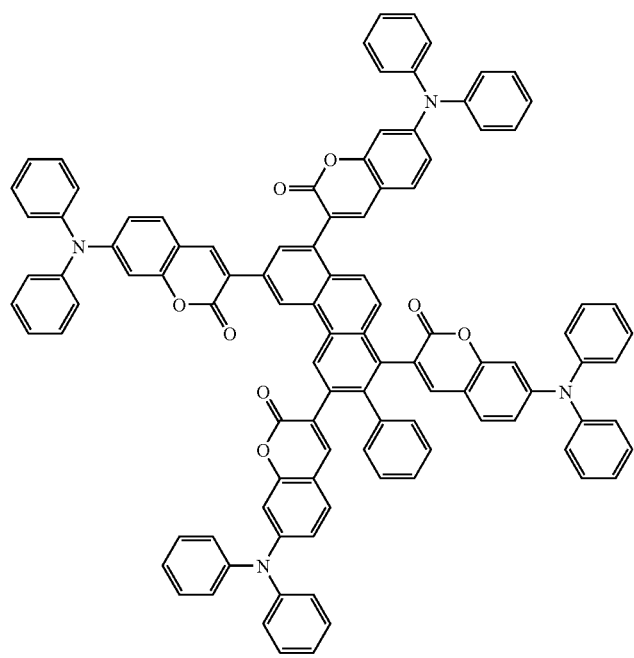
(1-26)

2. Explanation of Compounds Used for the Electron Transport Layer in the Organic Electroluminescent Device of the Present Invention Compounds used for the electron transport layer in the organic electroluminescent device of the present invention include the compounds represented by Formula (2), (3), (4), (5-1) or (5-2) described above. The respective compounds shall be explained below.

2-1. Explanation of the Compound Represented by Formula (2)

A compound used for the electron transport layer in the organic electroluminescent device of the present invention is the compound represented by Formula (2) described above. The compound represented by Formula (2) shall be explained below.

G in Formula (2) represents merely a bond or a linkage group of an n valence, and it represents, for example, an aromatic group or a heteroaromatic group of an n valence which is constituted by one or plural five-membered rings or six-membered rings and which may be substituted. The aromatic group or heteroaromatic group of an n valence means a residue obtained by removing n atoms of a hydrogen atom or a substituent from an optional aromatic hydrocarbon compound or heteroaromatic hydrocarbon compound and a combination thereof, and to be specific, it is a linkage group of an n valence which is an aromatic ring having n pieces of a bond.

The aromatic ring includes, for example, a benzene ring, a naphthalene ring, an anthracene ring, a fluorene ring, a biphenyl ring, a terphenyl ring, an azulene ring, a phenanthrene ring, a triphenylene ring, a pyrene ring, a crysene ring, a naphthacene ring, a perylene ring, a pentacene ring, a hexacene ring, a coronene ring, a trinaphthylene ring, a furan ring, a thiophene ring, a pyrrole ring, an imidazole ring, a pyrazole ring, a 1,2,4-triazole ring, a 1,2,3-triazole ring, an oxazole ring, a thiazole ring, an isooxazole ring, an isothiazole ring, a furazan ring, a pyridine ring, a pyrazine ring, a pyrimidine ring, a pyridazine ring, an indolizine ring, a quinoline ring, an isoindole ring, an indole ring, an isoquinoline ring, a phthalazine ring, a purine ring, a naphthyridine ring, a quinoxaline ring, a quinazoline ring, a cinnoline ring, a pteridine ring, a carbazole ring, a phenanthridine ring, an acridine ring, a perimizine ring, a phenanthroline ring, a phenazine ring, a phenalene ring and a silole ring. They each may have independently plural optional substituents, and the plural substituents may be condensed with each other to further form a ring(s).

It is more preferably a benzene ring, a naphthalene ring, an anthracene ring, a phenanthrene ring, a fluorene ring, a terphenyl ring, a biphenyl ring, a thiophene ring, a pyridine ring, a pyrazine ring, a pyrimidine ring, a phenalene ring, a silole ring or a pyridazine ring, and the above rings may be substituted. It is further preferably a benzene ring, a naphthalene ring, an anthracene ring, a phenanthrene ring, fluorene ring, a thiophene ring, a pyridine ring, a phenalene ring or a silole ring, and these rings may be substituted.

The "substituents" in "each may have independently plural optional substituents" include, for example, aliphatic hydrocarbon groups such as methyl, ethyl, propyl, isopropyl, s-butyl, t-butyl and pentyl, alicyclic hydrocarbon groups such as cyclopropyl, cyclobutyl, cyclopentyl, cyclohexyl and cycloheptyl, aromatic hydrocarbon groups such as phenyl, o-tolyl, m-tolyl, m-tolyl, xylyl, mesityl, o-cumenyl, m-cumenyl, p-cumenyl, naphthyl, anthracenyl, phenanthryl, biphenylyl, methylphenyl, ethylphenyl, butylphenyl, methylnaphthyl, dimethylnaphthyl, ethylnaphthyl, diethylnaphthyl and butylnaphthyl, heterocyclic groups such as pyridyl, quinazolyl, quinolyl, pyrimidinyl, pyrazinyl, pyridazinyl, furyl, thienyl, pyrrolyl, imidazolyl, tetrazolyl, thiazolyl, triazolyl, oxazolyl, oxadiazolyl, benzoxazolyl, benzothiazolyl, benzothienyl, carbazolyl and phenanthrolinyl, alkoxyl groups such as methoxy, ethoxy, propoxy, phenoxy and benzyloxy, and the like.

More preferred "substituent" is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthryl, benzoxazolyl, benzothiazolyl, benzothienyl or carbazolyl. Further preferred "substituent" is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl. The most preferred "substituent" is alkyl having 1 to 4 carbon atoms, phenyl, tolyl, xylyl, mesityl, naphthyl, ethylphenyl, methylnaphthyl, ethylnaphthyl or pyridyl.

G in Formula (2) includes, for example, the following groups. R in the structural formulas each represents independently hydrogen, methyl, ethyl, isopropyl, cyclohexyl, phenyl, 1-naphthyl or 2-naphthyl.

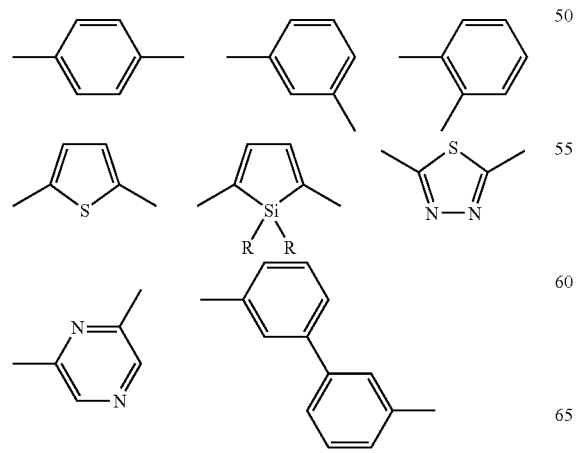

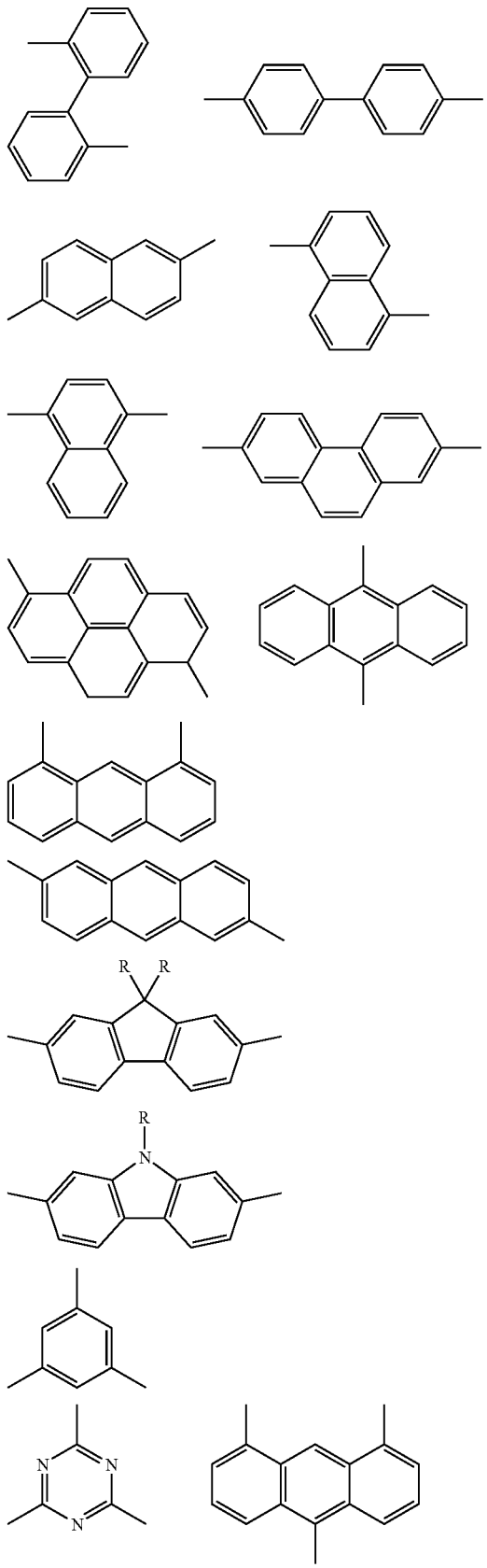

-continued

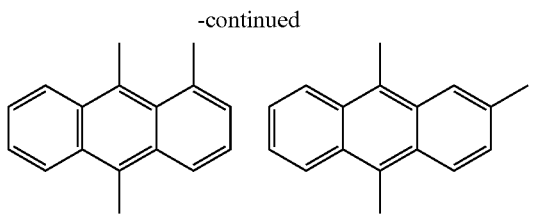
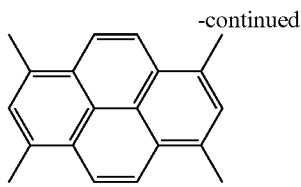
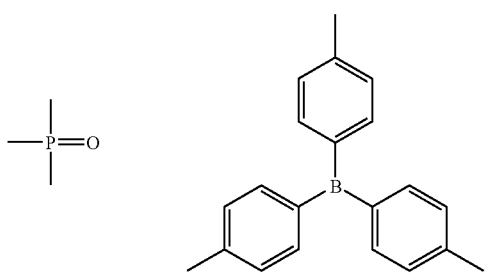
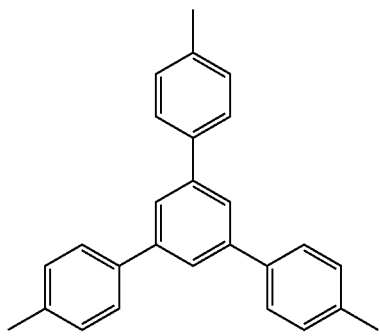
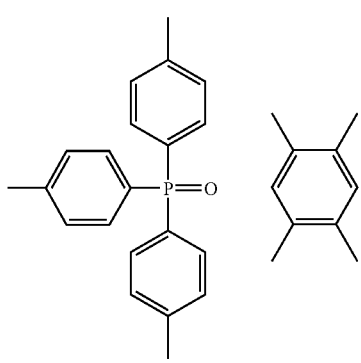
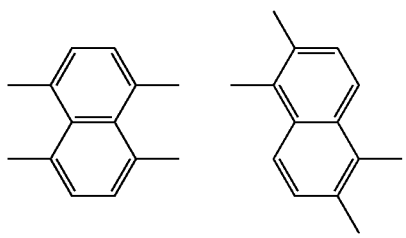
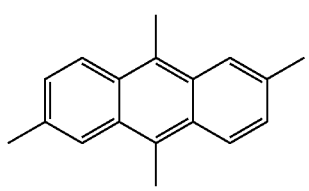

The number n in Formula (2) represents an integer of 2 to 8, preferably 2 to 6, more preferably 2 to 4, further preferably 2 or 3 and most preferably 2.

Alkyl which may be substituted, alkenyl which may be substituted, aryl which may be substituted, arylalkyl which may be substituted, arylalkenyl which may be substituted or cycloalkyl which may be substituted in $R^{11}$ to $R^{18}$ of Formula (2) includes the same ones as described in explains of $R^1$ to $R^4$ of Formula (1-Z), and the same ones are preferred.

"Heteroaryl" in "heteroaryl which may be substituted" in $R^{11}$ to $R^{18}$ of Formula (2) includes, for example, a heterocyclic group containing 1 to 5 hetero atoms selected from an oxygen atom, a sulfur atom and a nitrogen atom other than carbon atoms as a ring constituting atom. Paying attentions to a carbon atom which is the constituting atom other than the hetero atoms, it includes, for example, heteroaryl having 2 to 30 carbon atoms, preferably heteroaryl having 2 to 25 carbon atoms and more preferably heteroaryl having 2 to 20 carbon atoms. It includes, for example, furyl, thienyl, pyrrolyl, oxazolyl, isooxazolyl, thiazolyl, isothiszolyl, imidazolyl, pyrazolyl, oxadiazolyl, frazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathienyl, thianthrenyl, indolidinyl and phenanthrolinyl, and preferred are, for example, triazolyl, pyridyl, pyrimidinyl, pyridazinyl, pyrazinyl, benzo[b]thienyl, benzimidazolyl, quinolyl, isoquinolyl, carbazolyl and phenanthrolinyl.

"Boryl which may be substituted" in $R^{11}$ to $R^{18}$ of Formula (2) includes, to be specific, aryl boryl such as diphenylboryl, ditolylboryl, dimesitylboryl, dianthrylboryl and anthrylmesitylboryl, and among them, it includes diarylboryl and the like. A "substituent" in substituted boryl includes, for example, ortho-di-substituted phenyl. Specific "substituent" includes xylyl, mesityl, diisopropylphenyl, triisopropylphenyl, terphenyl and the like.

"Silyl which may be substituted" in $R^{11}$ to $R^{18}$ of Formula (2) includes, to be specific, alkylsilyl such as trimethylsilyl, t-butyldimethylsilyl, t-butyldiphenylsilyl and triphenylsilyl, and among them, it includes trialkylsilyl and alkoxysilyl such as trimethoxysilyl, triethoxysilyl and tributoxysilyl.

"Aralkyl" in "aralkyl which may be substituted" in $R^{11}$ to $R^{18}$ of Formula (2) includes aralkyl having 7 to 20 carbon atoms. Preferred "aralkyl" is aralkyl having 7 to 15 carbon atoms. More preferred "aralkyl" is aralkyl having 7 to 10 carbon atoms. Specific "aralkyl" includes benzyl, phenylethyl, methylbenzyl (tolubenzyl), naphthylmethyl (menaphthyl) and the like.

A "substituent" in $R^{11}$ to $R^{18}$ includes the same ones as described in explanations of $R^1$ to $R^4$ in Formula (1-Z). The preferred "substituent" is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl.

The compounds represented by Formula (2-1) or (2-2) described above can be given as further specific examples of the compound represented by Formula (2) described above. Explanations given in, for example, JP H15-123983 A/2003 can be quoted for explanation on the compound represented by Formula (2) described above.

2-2. Explanation of the Compound Represented by Formula (3)

A compound used for the electron transport layer in the organic electroluminescent device of the present invention is the compound represented by Formula (3) described above. The compound represented by Formula (3) shall be explained below.

Alkyl which may be substituted, alkenyl which may be substituted, aryl which may be substituted, arylalkyl which may be substituted, silyl which may be substituted, aralkyl which may be substituted or cycloalkyl which may be substituted in $R^{21}$ to $R^{26}$ of Formula (3) includes the same ones as described in explanations of $R^1$ to $R^4$ in Formula (1-Z) and explanations of $R^{11}$ to $R^{18}$ in Formula (2), and the same ones are preferred.

"Heteroaryl" in "heteroaryl which may be substituted" in $R^{21}$ to $R^{26}$ of Formula (3) includes, for example, a heterocyclic group containing 1 to 5 hetero atoms selected from an oxygen atom, a sulfur atom and a nitrogen atom other than carbon atoms as a ring constituting atom. Paying attentions to a carbon atom which is the constituting atom other than the hetero atoms, it includes, for example, heteroaryl having 2 to 30 carbon atoms, preferably heteroaryl having 2 to 25 carbon atoms and more preferably heteroaryl having 2 to 20 carbon atoms. It includes, for example, furyl, thienyl, pyrrolyl, oxazolyl, isooxazolyl, thiazolyl, isothiszolyl, imidazolyl, pyrazolyl, oxadiazolyl, frazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathienyl, thianthrenyl, indolidinyl and phenanthrolinyl, and preferred are, for example, triazolyl, pyridyl, pyrimidinyl, pyridazinyl, pyrazinyl, benzimidazolyl, benzothiazolyl, quinolyl, isoquinolyl, carbazolyl and phenanthrolinyl.

A "substituent" in $R^{21}$ to $R^{26}$ includes the same ones as described in explanations of $R^1$ to $R^4$ in Formula (1-Z). The preferred "substituent" is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl. The "substituent" in $R^{23}$ and $R^{24}$ is more preferably phenyl, pyridyl, pyrimidinyl, pyrazinyl, pyridazinyl, imidazolyl, quinolyl, phenanthrolinyl, benzothiazolyl or benzothienyl. The "substituent" in $R^{25}$ and $R^{26}$ is more preferably alkyl having 1 to 4 carbon atoms, phenyl, tolyl, xylyl, mesityl, naphthyl, methylnaphthyl, pyridyl or quinolyl.

Explanations given in, for example, JP H9-087616 A/1997 (Patent NO. 2918150) can be quoted for explanation on the compound represented by Formula (3) described above.

2-3. Explanation of the Compound Represented by Formula (4)

A compound used for the electron transport layer in the organic electroluminescent device of the present invention is the compound represented by Formula (4) described above. The compound represented by Formula (4) shall be explained below.

Alkyl which may be substituted, aryl which may be substituted, boryl which may be substituted, silyl which may be substituted, aralkyl which may be substituted or cycloalkyl which may be substituted in $R^{31}$ to $R^{40}$ of Formula (4) includes the same ones as described in explanations of $R^1$ to $R^4$ in Formula (1-Z) and explanations of $R^{11}$ to $R^{18}$ in Formula (2), and the same ones are preferred.

Heteroaryl which may be substituted in $R^{31}$ to $R^{40}$ of Formula (4) includes the same ones as described in explanations of $R^{21}$ to $R^{26}$ of Formula (3), and the same ones are preferred.

A "substituent" in $R^{31}$ to $R^{40}$ includes the same ones as described in explanations of $R^1$ to $R^4$ in Formula (1-Z). The preferred "substituent" is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl. The "substituent" in $R^{31}$ and $R^{32}$ is more preferably pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl.

2-4. Explanation of the Compounds Represented by Formulas (5-1) and (5-2)

A compound used for the electron transport layer in the organic electroluminescent device of the present invention is the compound represented by Formula (5-1) or (5-2) described above. The compound represented by Formula (5-1) or (5-2) shall be explained below.

G and n in Formula (5-2) includes the same ones as described in explanations of G and n in Formula (2), and the same ones are preferred.

Alkyl which may be substituted, alkenyl which may be substituted, aryl which may be substituted, arylalkyl which may be substituted, boryl which may be substituted, silyl which may be substituted, aralkyl which may be substituted or cycloalkyl which may be substituted in $R^{41}$ to $R^{48}$ of Formula (5-1) or (5-2) includes the same ones as described in explanations of $R^1$ to $R^4$ in Formula (1-Z) and explanations of $R^{11}$ to $R^{18}$ in Formula (2), and the same ones are preferred.

Heteroaryl which may be substituted in $R^{41}$ to $R^{48}$ of Formula (5-1) or (5-2) includes the same ones as described in explanations of $R^{11}$ to $R^{18}$ in Formula (2), and the same ones are preferred.

A "substituent" in $R^{41}$ to $R^{48}$ includes the same ones as described in explanations of $R^1$ to $R^4$ in Formula (1-Z). The preferred "substituent" is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl.

The compounds represented by Formula (5-1-1) described above can be given as further specific examples of the compound represented by Formula (5-1) or (5-2) described above. Explanations given in, for example, JP H15-123983 A/2003 and JP H17-108720 A/2005 can be quoted for explanation on the compound represented by Formula (5-1) or (5-2) described above.

3. Production Processes for the Compounds Described Above

Next, production processes for the compound represented by Formula (1) according to the present invention and the compound represented by Formula (2), (3), (4), (5-1) or (5-2) which can be applied as a material for the electron transport layer in the organic electroluminescent device shall be explained.

3-1. Production Process for the Compound Represented by Formula (1)

The compound represented by Formula (1) according to the present invention can be prepared by various processes, and if placing great importance on the economical efficiency, a process making use of dehydrocondensation reaction of an aldehyde group and an active methylene group is suited. When based on this process, a compound represented by Formula (1') shown below having φ corresponding to Formula (1) is reacted with a compound represented by Formula (1-Z') shown below having $R^1$ to $R^4$ corresponding to Formula (1) and an amino group, whereby the compound represented by Formula (1) can be produced at a good yield. In this respect, m in Formula (1') is the same integer as in Formula (1).

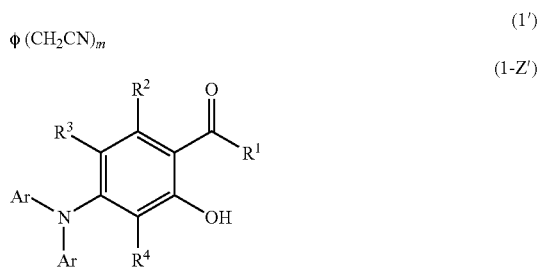

That is, appropriate amounts of the compounds represented by Formula (1') and Formula (1-Z') each are put in a reaction vessel and suitably dissolved, if necessary, in a solvent, and a base compound, an acidic compound and a Lewis acidic compound are added thereto. Then, they are reacted at ambient temperature or temperature exceeding the ambient temperature while heating and stirring by refluxing under heating and the like.

The base compound includes, for example, sodium hydroxide, potassium hydroxide, sodium carbonate, potassium carbonate, sodium hydrogencarbonate, sodium carbonate, ammonia, triethylamine, piperidine, pyridine, pyrrolidine, aniline, N,N-dimethylaniline and N,N-diethylaniline. The acidic compound includes, for example, hydrochloric acid, sulfuric acid, nitric acid, acetic acid, acetic anhydride, trifluoroacetic acid, p-toluenesulfonic acid, methanesulfonic acid and trifluoromethanesulfonic acid. The Lewis acidic compound includes, for example, aluminum chloride, zinc chloride, tin chloride and titanium tetrachloride.

The solvent includes, for example, hydrocarbons such as pentane, hexane, cyclohexane, octane, benzene, toluene and xylene, halides such as carbon tetrachloride, chloroform, 1,2-dichlorobenzene, 1,2-dibromobenzene, trichloroethylene, tetrachloroethylene, chlorobenzene, bromobenzene and α-dichlorobenzene, alcohols and phenols such as methanol, ethanol, 1-propanol, 2-propanol, 1-butanol, 2-butanol, isobutyl alcohol, isopentyl alcohol, cyclohexanol, ethylene glycol, propylene glycol, 2-methoxyethanol, 2-ethoxyethanol, phenol, benzyl alcohol, cresol, diethylene glycol, triethylene glycol and glycerin, ethers such as diethyl ether, diisopropyl ether, tetrahydrofuran, tetrahydropyran, 1,4-dioxane, anisole, 1,2-dimethoxyethane, diethylene glycol dimethyl ether, dicyclohexyl-18-crown-6, methyl carbitol and ethyl carbitol, acids and acid derivatives such as acetic acid, acetic anhydride, trichloroacetic acid, trifluoroacetic acid, propionic anhydride, ethyl acetate, butyl carbonate, ethylene carbonate, propylene carbonate, formamide, N-methylformamide, N,N-dimethylformamide, N-methylacetamide, N,N-dimethylacetamide, hexamethylphosphoric triamide and trimethyl phosphate, nitriles such as acetonitrile, propionitrile, succinonitrile and benzonitrile, nitro compounds such as nitromethane and nitrobenzene, sulfur-containing compounds such as dimethyl sulfoxide and sulfolane, water and the like. The above compounds are used, if necessary, in suitable combination.

In general, when using a solvent, an efficiency of reaction is reduced if an amount of the solvent is increased. On the other hand, if it is decreased, it is difficult to evenly heat and stir, or side reactions are liable to take place. Accordingly, an amount of the solvent is preferably up to 100 times, usually 5 to 50 times as large as the whole part of the raw material compounds in terms of a weight ratio. The reaction is completed within 10 hours, though depending on the kinds of the raw material compounds and the reaction conditions, usually 0.5 to 5 hours. Progress of the reaction can be monitored, for example, by a conventional method such as thin layer chromatography, gas chromatography and high performance liquid chromatography. The compound represented by Formula (1) can be produced in a desired amount by this process or according to this process. All of the compounds represented by Formula (1') and Formula (1-Z') can be obtained by conventional processes for preparing similar compounds, and when the commercial products are available, they may be used after suitably refined if necessary.

The compound represented by Formula (1) which is obtained by the process described above is usually refined prior to use by conventional methods for refining the similar compounds such as dissolution, separation, decantation, filtration, extraction, concentration, thin film chromatography, column chromatography, gas chromatography, high performance liquid chromatography, distillation, sublimation and crystallization, and these methods are applied by suitably combining. The compounds are preferably refined, though depending on the kinds of the compounds and the uses of the organic electroluminescent device, to a high degree usually prior to use by a method such as distillation, crystallization and/or sublimation.

Among them, sublimation is particularly excellent because of the reasons that it readily provides crystal of a high purity by single operation and decreases loss of the compound caused by operation and that it prevents a solvent from being introduced into the crystal. A sublimation method applied may be an atmospheric pressure sublimation method or a reduced pressure sublimation method, and the latter reduced pressure sublimation method is usually applied. When the compound represented by Formula (1) is sublimated under reduced pressure, a suitable amount of the compound is charged into a sublimation refining apparatus and heated at as low temperature as possible which is lower than a melting point so that the compound is not decomposed while maintaining the apparatus at a reduced pressure of lower than $10^{-2}$ Torr, preferably $10^{-3}$ Torr or lower. When the compound subjected to sublimation refining has a relatively low purity, the pressure reduction degree and the heating temperature are adjusted so that impurities are not mixed therein to thereby suppress the sublimation rate. Also, when the compound is less liable to be sublimated, inert gas such as rare gas is allowed to pass through the sublimation refining apparatus to thereby accelerate the sublimation. A size of the crystal obtained by the sublimation can be adjusted by controlling temperature on a condensing face in the sublimation refining apparatus. The condensing face is maintained at slightly lower temperature than the heating temperature to gradually crystallize the compound, whereby the relatively large crystal can be obtained.

3-2. Production Process for the Compound Represented by Formula (2), (3), (4), (5-1) or (5-2)

The compound represented by Formula (2), (3), (4), (5-1) or (5-2) can be produced by publicly known synthetic processes using publicly known compounds. It can be synthesized by a process described in a publicly known document (for example "Metal-Catalyzed Cross-Coupling Reactions—Second, Completely Revised and Enlarged Edition", "J. Am. Chem. Soc. (1996), 118, 11974" and the like) as one example of the production processes and by processes described in the examples of the present specification.

4. Organic Electroluminescent Device

The organic electroluminescent device according to the present invention is an organic electroluminescent device comprising a pair of electrodes comprising an anode and a cathode and an emission layer which is disposed between a pair of the above electrodes and which contains at least one of the compounds represented by Formula (1). Further, it is an organic electroluminescent device comprising, in a certain case, an electron transport layer containing at least one of the compounds represented by Formula (2), (3), (4), (5-1) or (5-2). The organic electroluminescent device according to the present embodiment shall be explained in details based on a drawing. FIG. 1 is an outline cross-sectional drawing showing the organic electroluminescent device according to the present invention.

<Structure of Organic Electroluminescent Device>

An organic electroluminescent device 100 shown in FIG. 1 comprises a substrate 101, an anode 102 provided on the substrate 101, a hole injection layer 103 provided on the anode 102, a hole transport layer 104 provided on the hole injection layer 103, an emission layer 105 provided on the hole transport layer 104, an electron transport layer 106 provided on the emission layer 105, an electron injection layer 107 provided on the electron transport layer 106 and a cathode 108 provided on the electron injection layer 107.

The organic electroluminescent device 100 may be turned upside down in a preparation order and may assume a structure in which it comprises the substrate 101, the cathode 108 provided on the substrate 101, the electron injection layer 107 provided on the cathode 108, the electron transport layer 106 provided on the electron injection layer 107, the emission layer 105 provided on the electron transport layer 106, the hole transport layer 104 provided on the emission layer 105, the hole injection layer 103 provided on the hole transport layer 104 and the anode 102 provided on the hole injection layer 103.

All the respective layers described above do not necessarily have to be present, and the hole injection layer 103, the hole transport layer 104, the electron transport layer 106 and the electron injection layer 107 are layers which are optionally provided, wherein a minimum structural unit assumes a structure comprising the anode 102, the emission layer 105 and cathode 108. The respective layers described above each may comprise a single layer or plural layers.

The mode of the layers constituting the organic electroluminescent device may be, in addition to the structural mode of "substrate/anode/hole injection layer/hole transport layer/emission layer/electron transport layer/electron injection layer/cathode described above", the structural modes of "substrate/anode/hole transport layer/emission layer/electron transport layer/electron injection layer/cathode", "substrate/anode/hole injection layer/emission layer/electron transport layer/electron injection layer/cathode" "substrate/anode/hole injection layer/hole transport layer/emission layer/electron injection layer/cathode", "substrate/anode/hole injection layer/hole transport layer/emission layer/electron injection layer/cathode", "substrate/anode/emission layer/electron transport layer/electron injection layer/cathode", "substrate/anode/hole transport layer/emission layer/electron injection layer/cathode", "substrate/anode/hole transport layer/emission layer/electron transport layer/cathode", "substrate/anode/hole injection layer/emission layer/electron injection layer/cathode", "substrate/anode/hole injection layer/emission layer/electron transport layer/cathode", "substrate/anode/hole injection layer/hole transport layer/emission layer/cathode", "substrate/anode/hole injection layer/emission layer/cathode", "substrate/anode/hole transport layer/emission layer/cathode", "substrate/anode/emission layer/electron transport layer/cathode", "substrate/anode/emission layer/electron injection layer/cathode" and "substrate/anode/emission layer/cathode".

<Substrate in the Organic Electroluminescent Device>

The substrate 101 is a base for the organic electroluminescent device 100, and quartz, glass, metal and plastics are usually used therefor. The substrate 101 is formed in the shape of a plate, a film or a sheet according to the purposes, and a glass plate, a metal plate, a metal flake, a plastic film or a plastic sheet is used. Among them, a glass plate and a plate made of a transparent synthetic resin such as polyester, polymethacrylate, polycarbonate and polysulfone are preferred. Soda lime glass, non-alkali glass and the like are used for the glass substrate. The thickness thereof may be such a thickness as enough for maintaining the mechanical strength, and therefore it is 0.2 mm or more. An upper limit value of the thickness is 2 mm or less, preferably 1 mm or less. The material of glass is preferably non-alkali glass since ions eluted from glass are preferably smaller. Soda lime glass which is provided with a barrier coat such as $SiO_2$ is commercially available, and therefore it can be used. The substrate 101 may be provided at least on one face thereof with a gas barrier film such as a minute silicon oxide film in order to enhance gas barrier property thereof. Particularly when a plate, a film or a sheet made of a synthetic resin having low gas barrier property is used for the substrate 101, a gas barrier film is preferably provided thereon.

<Anode in the Organic Electroluminescent Device>

The anode 102 plays a role of injecting holes into the emission layer 105. When the hole injection layer 103 and/or the hole transport layer 104 are provided between the anode 102 and the emission layer 105, holes are injected into the emission layer 105 via these layers.

A material for forming the anode 102 includes inorganic compounds and organic compounds. The inorganic compounds include, for example, metals (aluminum, gold, silver, nickel, palladium, chromium and the like), metal oxides (oxide of indium, oxide of tin, indium-tin oxide (ITO) and the like), halogenated metals (copper iodide and the like), copper sulfide, carbon black, ITO glass, nesa glass and the like. The organic compounds include, for example, polythiophene such as poly(3-methylthiophene) and electrically conductive polymers such as polypyrrole, polyaniline and the like. In addition thereto, those suitably selected from materials used for an anode of an organic electroluminescent device can be used.

A resistance of the transparent electrode shall not be restricted as long as an electric current sufficient for emission of the light emitting device can be supplied, and it is preferably a low resistance from the viewpoint of power consumption of the light emitting device. For example, an ITO substrate having a resistance of 300 Ω/square or less functions as a device electrode. At present, a substrate having a resistance of about 10 Ω/square can be supplied, and therefore a product having a low resistance of 100 to 5 Ω/square, preferably 50 to 5 Ω/square is particularly preferably used. A thickness of ITO can optionally be selected depending on a resistance value thereof, and it is usually used in a range of 100 to 300 nm in many cases.

<Hole Injection Layer and Hole Transport Layer in the Organic Electroluminescent Device>

The hole injection layer 103 plays a role of efficiently injecting holes moving from the anode 102 into the emission layer 105 or the hole transport layer 104. The hole transport layer 104 plays a role of efficiently transporting holes injected from the anode 102 or holes injected from the anode 102 via the hole injection layer 103 into the emission layer 105. The hole injection layer 103 and the hole transport layer 104 are formed respectively by laminating or mixing at least one of hole injecting and transporting materials or from a mixture of the hole injecting and transporting material with a high molecular binder. Further, inorganic salt such as iron chloride (III) may be added to the hole injecting and transporting material to form the layers.

The hole injecting and transporting material has to efficiently inject and transport holes from a positive electrode between the electrodes to which an electrical field is applied, and it is desirable that the hole injection efficiency is high and that the holes injected are efficiently transported. Accordingly, preferred is the material which has small ionization potential and large hole mobility and in which impurities trapped are less liable to be generated in producing and using.

Optional compounds selected from compounds which have so far conventionally been used as an electron transport material of a hole in a photoconductive material, p type semiconductors and publicly known compounds used for a hole injection layer and a transport layer in an organic electroluminescent device can be used as materials for forming the hole injection layer 103 and the hole transport layer 104. The specific examples thereof are preferably carbazole derivatives (N-phenylcarbazole, polyvinylcarbazole and the like), bis-carbazole derivatives such as bis(N-allylcarbazole) and bis (N-alkylcarbazole), triarylamine derivatives (polymers having aromatic tertiary amine on a principal chain or a side chain), triphenylamine derivatives such as 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl, N,N'-diphenyl-N,N'-di(3-methylphenyl)-4,4'-diphenyl-1,1'-diamine, N,N'-dinaphthyl-N,N'-diphenyl-4,4'-diphenyl-1,1'-diamine and 4,4',4''-tris(3-methylphenyl(phenyl)-amino)triphenylamine, star burst amine derivatives and the like, stilbene derivatives, heterocyclic compounds such as phthalocyanine derivatives (non-metal phthalocyanines, copper phthalocyanine and the like), pyrazoline derivatives, hydrazone compounds, benzofuran derivatives, thiophene derivatives, oxadiazole derivatives and porphylin derivatives, polysilane and the like. In polymer compounds, polycarbonate, styrene derivatives, polyvinylcarbazole, polysilane and the like which have the monomers described above on side chains are preferred, but they shall not specifically be restricted as long as they are compounds which can form a thin film necessary for preparing a light emitting device and which can inject holes from an anode and can transport the holes.

It is know as well that an electrical conductivity of an organic semiconductor is strongly influenced by doping thereof. Such organic semiconductor matrix substance is constituted from a compound having good electron donating property or a compound having good electron accepting property. Strong electron acceptors such as tetracyanoquinonedimethane (TCNQ) or 2,3,5,6-tetrafluorotetracyano-1,4-benzoquinonedimethane (F4TCNQ) are known for doping electron donating substances (refer to, for example, a document "M. Pfeiffer, A. Beyer, T. Fritz, K. Leo, Appl. Phys. Lett., 73 (22), 3202 to 3204 (1998)" and a document "J. Blochwitz, M. Pfeiffer, T. Fritz, K. Leo, Appl. Phys. Lett., 73 (6), 729 to 731 (1998)"). They produce so-called holes by an electron moving process in an electron donating type base material (hole transport material). Conductivity of the base material is changed to a considerably large extent by the number and mobility of holes. Known as a matrix substance having hole transport property are, for example, benzidine derivatives (TPD and the like), starburst amine derivatives (TDATA and the like) and specific metal phthalocyanines (particularly zinc phthalocyanine and the like) (JP H17-167175 A/2005).

<Emission Layer in the Organic Electroluminescent Device>

The emission layer 105 may comprise either a single layer or plural layers and is formed by an emission material (host material and dopant material). The dopant material may be contained in either the whole part or a part of the host material. A too large amount of the dopant material brings about a concentration quenching phenomenon, and therefore it is used in an amount of preferably 10 to 1% by weight, more preferably 5 to 2% by weight based on the host material. In a doping method, the emission layer can be formed by a method of co-depositing with the host material, or the dopant material may be mixed in advance with the host material and then deposited at the same time.

The host material shall not specifically be restricted, and suitably used are condensed ring derivatives such as anthracene and pyrene which have so far been known as an emission material, metal chelated oxynoide compounds, bis-styryl derivatives such as bisstyrylanthracene derivatives and distyryl benzene derivatives, tetraphenylbutadiene derivatives, coumarin derivatives, oxadiazole derivatives, pyrrolopyridine derivatives, perinone derivatives, cyclopentadiene derivatives, oxadiazole derivatives, thiadiazolopyridine derivatives, pyrrolopyrrole derivatives and polymers such as polyphenylene vinylene derivatives, polyparaphenylene derivatives and polythiophene derivatives.

In addition to the above compounds, compounds suitably selected from compounds described in Kagaku Kogyo (Chemical Industry) issued in June 2004, pp. 13, reference documents quoted therein and the like can be used as the host material.

The compound represented by Formula (1) described above can be used as the dopant material. A content of the compound represented by Formula (1) as the dopant material in the emission layer 105 is preferably 1 to 50% by weight, more preferably 1 to 20% by weight, particularly preferably 1 to 10% by weight and most preferably 1 to 5% by weight.

<Electron Injection Layer and Electron Transport Layer in the Organic Electroluminescent Device>

The electron injection layer 107 plays a role of efficiently injecting electrons moving from the cathode 108 into the emission layer 105 or the electron transport layer 106. The electron transport layer 106 plays a role of efficiently transporting electrons injected from the cathode 108 or electrons injected from the cathode 108 via the electron injection layer 107 into the emission layer 105. The electron transport layer 106 and the electron injection layer 107 are formed respectively by laminating or mixing at least one of electron transporting and injecting materials or from a mixture of the electron transporting and injecting material with a high molecular binder.

An electron injection and transport layer is a layer for controlling injection of electrons from the cathode and transportation of the electrons, and it is desirable that the electron injection efficiency is high and that the electrons injected are efficiently transported. Accordingly, preferred is the material which has large electron affinity and large electron mobility and is excellent in stability and in which impurities trapped are less liable to be generated in producing and using. However, when considering a transport balance between a hole and an electron, the material is provided, even if electron transport ability is not so high, with an effect of enhancing luminous efficiency to the same extent as that of a material having high electron transport ability in the case of playing principally a role of efficiently inhibiting holes coming from the anode from moving to a cathode side without recombination. Accordingly, a function of a layer which can efficiently inhibit holes from moving may be included as well in the electron injection and transport layer in the present embodiment.

The compound represented by Formula (2), (3), (4), (5-1) or (5-2) described above can be used as a material for forming the electron transport layer 106 and the electron injection layer 107. Compounds disclosed in JP H15-123983 A/2003 and JP H17-108720 A/2005 can be given as the specific examples of the compound represented by Formula (2), (3), (4), (5-1) or (5-2) described above. A content of the compound represented by Formula (2), (3), (4), (5-1) or (5-2) described above in the electron transport layer 106 or the electron injection layer 107 is preferably 1 to 100% by weight, more preferably 10 to 100% by weight, particularly preferably 50 to 100% by weight and most preferably 80 to 100% by weight.

A case in which an organic fluorescent compound having a phenanthroline skeleton represented by Formula (5-1) or (5-2) described above is used for the electron transport layer shall be explained. A material which is excellent in thermal stability and ability to form a thin film is desired for obtaining stable emission over a long period of time. Among the organic fluorescent compounds having a phenanthroline skeleton, preferred are compounds in which a substituent itself has a three-dimensional steric structure or which are provided with a three-dimensional steric structure by steric repulsion against the phenanthroline skeleton or an adjacent substituent and compounds in which plural phenanthroline skeletons are combined. Further, when combining plural phenanthroline skeletons, more preferred are compounds containing a conjugated bond, a substituted or non-substituted aromatic hydrocarbon and a substituted or non-substituted aromatic heterocycle in a combined unit.

<Cathode in the Organic Electroluminescent Device>

The cathode 108 plays a role of injecting electrons into the emission layer 105 via the electron injection layer 107 and the electron transport layer 106.

A material for forming the cathode 108 shall not specifically be restricted as long as it is a material which can efficiently inject electrons into the organic layers, and the same materials as the materials for forming the anode 102 can be used. Among them, preferred are metals such as tin, magnesium, indium, calcium, aluminum, silver, copper, nickel, chromium, gold, platinum, iron, tin, zinc, lithium, sodium, potassium, cesium and magnesium and alloys thereof (magnesium-silver alloys, magnesium-indium alloys and aluminum-lithium alloys such as lithium fluoride/aluminum alloys). Lithium, sodium, potassium, cesium, calcium, magnesium and alloys containing the above metals having a low work function are effective for elevating the electron injection efficiency to enhance the device characteristics. However, the above metals having a low work function are usually instable in the air in many cases, and a method in which a small amount of lithium, cesium and magnesium (1 nm or less in terms of a film thickness formed by vacuum deposition) is doped to use an electrode having high stability can be given as the preferred method. Inorganic salts such as lithium fluoride, cesium fluoride, lithium oxide and cesium oxide can be used as well, and therefore it shall not specifically be restricted to the above materials.

Further, a preferred example for protecting the electrodes includes lamination of metals such as platinum, gold, silver, copper, iron, tin, aluminum and indium, alloys using these metals, inorganic substances such as silica, titania and silicon nitride, polyvinyl alcohol, polyvinyl chloride and hydrocarbon high molecular compounds. A method for preparing the above electrodes shall not specifically be restricted to resistance heating, electron beam, sputtering, ion plating, coating and the like as long as the electrodes can conduct electricity.

<Binder which May be Used in the Respective Layers>

The materials used for the hole injection layer, the hole transport layer, the emission layer, the electron transport layer and the electron injection layer each described above can form alone the respective layers, and the materials which are dispersed in solvent-soluble resins such as polyvinyl chloride, polycarbonate, polystyrene, poly(N-vinylcarbazole), polymethyl methacrylate, polybutyl methacrylate, polyester, polysulfone, polyphenylene oxide, polybutadiene, hydrocarbon resins, ketone resins, phenoxy resins, polysulfone, polyamide, ethyl cellulose, vinyl acetate, ABS resins and polyurethane resins; curing resins such as phenol resins, xylene resins, petroleum resins, urea resins, melamine resins, unsaturated polyester resins, alkyd resins, epoxy resins and silicon resins; and the like as high molecular binders can be used as well.

<Preparing Method for the Organic Electroluminescent Device>

The respective layers constituting the organic electroluminescent device can be formed by forming thin films from the materials for constituting the respective layers by methods such as a deposition method, resistance heating deposition, electron beam deposition, sputtering, a molecular lamination method, a printing method, a spin cast method, a cast method and a coating method. The film thicknesses of the respective layers thus formed shall not specifically be restricted and can suitably be set according to the properties of the materials, and they fall usually in a range of 2 to 5000 nm. The film thickness can usually be measured by means of a quartz oscillation type film thickness measuring apparatus and the like. When a thin film is formed by a deposition method, deposition conditions thereof are varied depending on the kind of the materials, the crystal structure and the aggregate structure which are aimed by the film, and the like. In general, the deposition conditions can suitably be set preferably in the ranges of a boat heating temperature of 50 to 400° C., a vacuum degree of $10^{-6}$ to $10^{-3}$ Pa, a deposition rate of 0.01 to 50 nm/second, a substrate temperature of −150 to +300° C. and a film thickness of 2 nm to 5 μm.

Next, a preparing method for an organic electroluminescent device comprising an anode/a hole injection layer/a hole transport layer/an emission layer comprising a host material and a dopant material/an electron transport layer/an electron injection layer/a cathode shall be explained as one example of a preparing method for the organic electroluminescent device. A thin film of an anode material is formed on a suitable substrate by a deposition method and the like to prepare an anode, and then the thin films of a hole injection layer and a hole transport layer are formed on the above anode. A host material and a dopant material are co-deposited thereon to form a thin film, whereby an emission layer is prepared, and an electron transport layer and an electron injection layer are formed on the above emission layer. Further, a thin film comprising a substance for a cathode is formed thereon by a deposition method and the like to prepare a cathode, whereby the targeted organic electroluminescent device is obtained. In preparing the organic electroluminescent device described above, the preparing order can be turned upside down to prepare it as well in the order of the cathode, the electron injection layer, the electron transport layer, the emission layer, the hole transport layer, the hole injection layer and the anode.

When direct voltage is applied to the organic electroluminescent device thus obtained, it may be applied with the anode being set to a polarity of + and the cathode being set to a polarity of −, and when a voltage of 2 to 40 V is applied, emission can be observed from a transparent or translucent electrode side (the anode or the cathode and both). This organic electroluminescent device emits light as well when applying a pulse current and an alternating current. A waveform of the alternating current applied may be optional.

<Application Examples of the Organic Electroluminescent Device>

The present invention can be applied as well to display units equipped with an organic electroluminescent device, lighting instruments equipped with an organic electroluminescent device and the like.

The display units or lighting instruments equipped with an organic electroluminescent device can be produced by such publicly known methods that the organic electroluminescent device according to the present embodiment is connected with publicly known drive apparatuses, and they can be driven by suitably using publicly known drive methods such as direct current drive, pulse drive and alternating current drive.

The display unit includes, for example, panel displays such as color flat panel displays and flexible displays such as flexible color electroluminescent (EL) displays (refer to, for example, JP H10-335066 A/1998, JP H15-321546 A/2003 and JP H16-281086 A/2004). A display system of the displays includes, for example, a matrix display system and/or a segment display system. A matrix display system and a segment display system may be coexistent in the same panel.

A matrix means a state in which pixels for display are two-dimensionally arranged in a lattice form, a mosaic form and the like, and characters and images are displayed by aggregate of the pixels. The form and the size of the pixels are determined by applications. For example, square pixels having a side of 300 μm or less are usually used for display of images and characters in personal computers, monitors and TV. In the case of a large-sized display such as display panels, pixels having a side of mm order are used. In the case of monochrome display, pixels having the same color are arranged, and in the case of color display, red, green and blue pixels are arranged for display. In this case, to be typical, a delta type and a stripe type are available. A drive method of this matrix may be either a linear sequential drive method and an active matrix. The linear sequential drive method has the advantaged that it has a simpler structure. However, considering the operation characteristics, the active matrix is more excellent in a certain case, and therefore this has to be used separately depending on the applications.

In the segment system (type), patterns are formed so that informations determined in advance are displayed, and light is emitted in a determined area. It includes, for example, display of time and temperature in digital watches and thermometers, display of operation states in audio instruments and electromagnetic cookers and display of panels in automobiles.

A lighting instrument includes, for example, lighting instruments such as indoor lighting instruments and backlights for liquid crystal displays (refer to, for example, JP H15-257621 A/2003, JP H15-277741 A/2003 and JP H16-119211 A/2004). The backlights are used principally for a purpose of enhancing a visibility of display equipments which do not spontaneously emit light, and they are used for liquid crystal displays, watches, audio instruments, car panels, display boards, indicators and the like. In particular, considering that backlights of a conventional system for uses in liquid crystal displays, especially, personal computers in which a reduction in a size is a problem comprise fluorescent lumps and optical waveguides, so that it is difficult to make them thin-shaped, a backlight using the light emitting device according to the present embodiment is characterized by that it is thin-shaped and lightweight.

As described above, the compound represented by Formula (1) described above according to the present invention can be applied, for example, as a material for a light emitting device such as an organic electroluminescent device. Further, the compound represented by Formula (1) has a characteristic of absorbing visible light. Accordingly, it can be applied to other applications such as light absorbing materials which cut off transmittance of light and make use of energy thereof. This light absorbing material is very useful for a wide variety of the fields including, for example, information recording, printing, print circuits, solar energy generation, electric machines and appliances, electric communication appliances, optical instruments, cloths, bed clothing products, products for health and agricultural materials.

In the field of information recording, the compound represented by Formula (1) is useful as a photographic material. Further, the compound represented by Formula (1) absorbs visible light, and therefore it is useful as a polymerizable compound used for optical cards, plate making, heat transfer recording, thermosensitive recording and the like. Also, the compound represented by Formula (1) is useful as a sensitizer and a photothermal exchanging agent for accelerating polymerization by sensitizing a polymerization initiator and the like.

Among the compounds represented by Formula (1), the compound in which an absorption maximum wavelength is close to an oscillation wavelength of a general-purpose visible light laser having an oscillation line in the vicinity of a wavelength of 500 nm (to be detailed, 450 to 550 nm) is useful as a photosensitizer for a photopolymerizable composition using a visible light laser having the above oscillation wavelength, a mercury lamp, a metal halide lamp, a xenon lamp or the like as an exposure light source. The above visible light laser includes, for example, gas lasers such as an argon ion laser, a krypton ion laser and a helium and neon laser, semiconductor lasers such as a CdS laser and solid lasers such as a distributed feedback type or Bragg reflection type Nd-YAG laser.

The above photosensitizer is very useful in the field of information recording in a thin film hologram, a volume hologram, an optical recording medium or the like. Further, it is very useful as well in the field of printing such as offset reproduction, photogravure engraving, screen plate making, direct plate making, digital direct plate making or flexographic plate making. Also, it is very useful as well in the field of printed circuit such as an etching resist ink, a plating resist ink, a solder resist ink and a character ink. Further, it is very useful as well in the field of electrophotography such as a copying machine, a facsimile or a printer. Also, it is very useful as well in the field of optical wiring such as optical surface mounting technology (optical SMT) and self-forming connection technology (optical soldering), and it is very useful as well in the various fields such as paints adhesives, packaging materials and dental forming materials.

In another application of the above photosensitizer, the compound represented by Formula (1) can be used, for example, in the field of solar energy generation by carrying on a semiconductor electrode of a pigment-sensitizing wet solar battery. In the above application, a sensitivity of a semiconductor electrode to visible light can be enhanced, and a photoelectric conversion efficiency of a solar battery can notably be improved. The compound represented by Formula (1) has practically trouble-free light fastness to environment light such as natural light and artificial light. Accordingly, a solar battery in which the compound represented by Formula (1) is used as a photosensitizer has the actual advantage that it is less liable to bring about a reduction in an electromotive force originating in the photosensitizer even when used for long time.

In the fields of electric communication appliances, electric machines and appliances and optical instruments, the compound represented by Formula (1) can be applied as a filtering material. In this case, it has the actual advantages that light having some hue can be cut off or converted to light having a different hue and that noises originating in visible light can be reduced. Further, it has the actual advantages that a rise in ambient temperature caused by radiant heat and the like can be reduced and that the visibility can be controlled to a desired level. The filtering material includes, for example, color filters, color conversion filters, image pickup tubes, semiconductor light-sensitive elements and optical fibers.

In another application of the above filtering material, it can be used, for example, in the field of agricultural materials by coating on a plastic base material for vinyl houses which is formed in the shape of sheet or a film and a glass plate for greenhouses. In this application, a wavelength distribution of light reaching useful plants such as ornamental plants, garden plants, edible plants and medical plants including fruits, cereal grains, vegetables and flowers is controlled to make it possible to regulate growth of the plants.

Further, a light shielding agent, a heat ray shielding agent, a heat insulating agent, a heat insulating energy storage agent and the like can be prepared by adding, if necessary, one or plural kinds of other materials absorbing light in a UV region, a visible region and/or an infrared region to the compound represented by Formula (1). In this application, it can be applied to general purpose clothing materials, particularly for example clothing materials using heat insulating energy storage fibers and fibers having a disguised performance against surveillance by a UV ray, a visible light, an infrared ray and the like.

The light shielding agent, the heat ray shielding agent, the heat insulating agent and the heat insulating energy storage agent each described above can be applied as well to, for example, drapes, pleats, shirring, races, casement, print, Venetian•blind, roll•screen, roman•shade, shatters, store curtains, blankets, futons, ticking, futon covers, sheets, cushions, pillows, pillow covers, mats, carpets, sleeping bags, interior materials for automobiles and construction products such as window glass and the like in addition to the clothing materials. Also, they can be applied as well to health products such as paper diaper, paper diaper cover, spectacles, products for health such as monocle and lorgnette, shoe socking, shoe lining, bag fabrics, wrapping cloths, umbrella fabrics, parasol, plushie (nuigurumi) or the like.

The above light shielding agent, heat ray shielding agent, heat insulating agent and heat insulating energy storage agent can be applied for example as well to lighting instruments and filters, panels and screens for information display equipments which are used for Braun tube display, liquid crystal display, plasma display and the like. Also, they can be applied as well to inspection windows of gas ranges, electric ranges, microwave ranges, ovens and the like, dark glasses, sun visors, sunroofs and the like. Further, they can be applied as well to packaging materials, filling materials, vessels and the like which are used for packaging, filling or receiving the articles described above.

In the above applications, an unnecessary change in temperature can be prevented and reduced, and disturbances and inconveniences caused by environment light (natural light, artificial light and the like) in organisms and articles including asthenopia, aging in visual cells and cataract which originate in excess visual light can be prevented and reduced. Further, a chromaticity, a color tone, a color, a texture or the like of articles can be adjusted, and reflected light and transmitted light from articles can be adjusted to a desired color balance.

Further, the compound represented by Formula (1) can be applied, like publicly known organic pigment compounds absorbing visible light, to inks for preventing alteration, bar code inks for preventing alteration and falsification, light absorbing inks, light absorbing paints, marking agents for determining positions of photographs and films, dyeing agents for assortment in recycling plastics, preheating auxiliary agents used in molding PET bottles, and the like. Further, it can be used as an active ingredient of drugs for treating ordinary tumors which are sensitive to visual light and a component for aiding the functions of the active ingredient.

The compound represented by Formula (1) emits fluorescent light and the like in a visible region by excitation. Accordingly, in addition to various applications as the light absorbing materials described above, it is also useful as, for example, a fluorescent brightening agent and a laser action substance in pigment laser which require an organic compound exhibiting emission ability.

When the compound represented by Formula (1) is used for a pigment laser, it may be used in the same manner as in a case where a publicly known pigment laser emission equipment is constituted. That is, the compound represented by Formula (1) is refined and dissolved in a suitable solvent, and an appropriate amount of a triplet quenching agent is added, if necessary, thereto. A pH of the solution is controlled to a suited level, and the solution is filtered and then filled in a pigment cell in a laser emission equipment. In this case, used as the triplet quenching agents are, for example, cycloheptatriene compounds, cyclooctatetraene compounds, piperidine compounds, benzophenone compounds and benzotriazole compounds.

In the compound represented by Formula (1), amplification gain is obtained in a very broad wavelength area in a visible region, and the emission wavelength can be changed to a large extent by changing a pH of the solvent. Further, it has the characteristics that it has a large heat resistance and a large light fastness as compared with those of publicly known similar compounds and that it is less liable to be deteriorated after used for long time. Accordingly, use of the compound represented by Formula (1) makes it possible to structure a narrow band pigment laser which emits light at an optional wavelength in a very broad wavelength area extending from a UV region to an infrared region. In this structure, one or plural kinds of other organic pigment compounds which function as a laser action substance are preferably used, if necessary, in combination, and suited narrow band technology is preferably applied. Such variable wavelength pigment laser is useful, for example, as a laser source in so-called picosecond-femtosecond analysis in the field of spectrometric analysis and separation of isotopes such as plutonium and uranium by a laser method.

A little special application making use of an absorbance of the compound represented by Formula (1) includes application to qualitative analysis and quantitative analysis which make use of peculiar reaction observed between materials originating in living organisms. The peculiar reaction observed between materials originating in living organisms includes, for example, enzymatic reaction, antigen-antibody reaction, signal transfer in an inside and an outside of a cell, complex formation between proteins and hybridization between protein and nucleic acid or nucleic acids. In the above qualitative analysis and quantitative analysis, the compound represented by Formula (1) can be used as an emission agent for labeling enzymes, matrixes, antigens, antibodies, soluble acceptors, proteins, glycolipids, nucleic acids or the like. Biological materials labeled with the compound represented by Formula (1) are very useful, for example, as a biological sensor in the fields of research and diagnosis.

EXAMPLES

The respective examples shall be shown below in order to explain the present invention in further details, but the present invention shall not be restricted thereto.

<Production Examples of a Compound for an Emission Layer and a Compound for an Electron Transport Layer>

Compound represented by Formula (1-1) Described Above:

A production process for the compound represented by Formula (1-1) described above shall be explained. Hereinafter, the present compound shall be called "BD".

N,N-diphenylaminosalicylaldehyde 2.89 g and m-phenylenediacetonitrile 0.78 g were charged into xylene 10 ml, and acetic acid and piperidine were further added thereto to react them by heating and refluxing on an oil bath. After left cooling, methanol was added and heated while stirring, and the resulting product was filtered under suction. This product was dried to obtain 4.8 g of a crude product. The crude product was refined by silica gel, and then the principal component was concentrated in one lot to obtain 0.78 g (yield: 22.4%) of the targeted compound.

A dichloromethane solution of the above compound was prepared, and absorption and fluorescence spectra thereof were measured to result in finding that maximum wavelengths were shown in 411 nm and 510 nm respectively. In this respect, the molar absorbance coefficient ($\epsilon$) was 7.05× $10^4$. Further, the compound had a melting point of 152° C. and a glass transition point (Tg) of 136° C. An NMR spectrum ($\delta$ (ppm), TMS) in heavy chloroform was: 6.86 to 6.91 (m, 4H), 7.14 to 7.20 (m, 12H), 7.31 to 7.40 (m, 10H), 7.47 (t, 1H), 7.69 (dd, 2H), 7.79 (s, 2H), 7.98 (t, 1H).

Compound Represented by Formula (1-2) Described Above:

A production process for the compound represented by Formula (1-2) described above shall be explained.

"p-Phenylenediacetonitrile" was used in place of "m-phenylenediacetonitrile" in the production process for the compound represented by Formula (1-1) described above to carry out reaction. That is, N,N-diphenylaminosalicylaldehyde 3.0 g and p-phenylenediacetonitrile 0.78 g were used to carry out synthesis in the same manner as in the production process for the compound represented by Formula (1-1) described above, and 1.96 g (yield: 56%) of the targeted compound was obtained.

A dichloromethane solution of the above compound was prepared, and absorption and fluorescence spectra thereof were measured to result in finding that maximum wavelengths were shown in 429 nm and 510 nm respectively. In this respect, the molar absorbance coefficient ($\epsilon$) was 7.38× $10^4$. Further, the compound had a melting point of 269° C. and a glass transition point (Tg) of 136° C. An NMR spectrum ($\delta$ (ppm), TMS) in heavy chloroform was: 6.87 to 6.91 (m, 4H), 7.14 to 7.19 (m, 12H), 7.31 to 7.37 (m, 10H), 7.75 (s, 2H), 7.76 (s, 6H).

Compound Represented by Formula (1-3) Described Above:

A production process for the compound represented by Formula (1-3) described above shall be explained.

"1,3,5-Tris(cyanomethyl)benzene" was used in place of "m-phenylenediacetonitrile" in the production process for the compound represented by Formula (1-1) described above to carry out reaction. That is, N,N-diphenylaminosalicylaldehyde 3.0 g and 1,3,5-tris(cyanomethyl)benzene 0.65 g were used to carry out synthesis in the same manner as in the production process for the compound represented by Formula (1-1) described above, and 0.93 g (yield: 27.9%) of the targeted compound was obtained.

A dichloromethane solution of the above compound was prepared, and absorption and fluorescence spectra thereof were measured to result in finding that maximum wavelengths were shown in 416 nm and 514 nm respectively. In this respect, the molar absorbance coefficient ($\epsilon$) was 11.03× $10^4$. Further, the compound had a melting point of 194° C. and a glass transition point (Tg) of 183° C. An NMR spectrum ($\delta$ (ppm), TMS) in deuterated chloroform was: 6.86 to 6.92 (m, 6H), 7.14 to 7.20 (m, 18H), 7.32 to 7.37 (m, 15H), 7.87 (s, 3H), 8.04 (s, 3H).

Compound Represented by Formula (1-4) Described Above:

A production process for the compound represented by Formula (1-4) described above shall be explained.

"N-phenyl,N-naphthylaminosalicylaldehyde" was used in place of "N,N-diphenylaminosalicylaldehyde" in the production process for the compound represented by Formula (1-1) described above to carry out reaction. That is, N-phenyl,N-naphthylaminosalicylaldehyde 4.35 g and m-phenylenediacetonitrile 1.00 g were used to carry out synthesis in the same manner as in the production process for the compound represented by Formula (1-1) described above, and 1.20 g (yield: 23.4%) of the targeted compound was obtained.

A dichloromethane solution of the above compound was prepared, and absorption and fluorescence spectra thereof were measured to result in finding that maximum wavelengths were shown in 407 nm and 508 nm respectively. In this respect, the molar absorbance coefficient (ε) was 7.55× $10^4$. Further, the compound had a melting point of 205° C. and a glass transition point (Tg) of 156° C. An NMR spectrum (δ (ppm), TMS) in deuterated chloroform was: 6.76 to 6.80 (m, 4H), 7.06 to 7.14 (m, 2H), 7.26 to 7.38 (m, 10H), 7.40 to 7.54 (m, 9H), 7.65 to 7.68 (m, 2H), 7.75 (s, 2H), 7.84 to 7.94 (m, 7H).

Compound Represented by Formula (1-5) Described Above:

A production process for the compound represented by Formula (1-5) described above shall be explained.

"N-phenyl,N-naphthylaminosalicylaldehyde" was used in place of "N,N-diphenylaminosalicylaldehyde" in the production process for the compound represented by Formula (1-2) described above to carry out reaction. That is, N-phenyl,N-naphthylaminosalicylaldehyde 4.35 g and p-phenylenediacetonitrile 1.00 g were used to carry out synthesis in the same manner as in the production process for the compound represented by Formula (1-2) described above, and 0.75 g (yield: 14.6%) of the targeted compound was obtained.

A dichloromethane solution of the above compound was prepared, and absorption and fluorescence spectra thereof were measured to result in finding that maximum wavelengths were shown in 423 nm and 503 nm respectively. In this respect, the molar absorbance coefficient (ε) was 8.38× $10^4$. Further, the compound had a melting point of 299° C. and a glass transition point (Tg) of 154° C. An NMR spectrum (δ (ppm), TMS) in deuterated chloroform was: 6.72 to 6.80 (m, 4H), 7.12 to 7.14 (m, 2H), 7.26 to 7.34 (m, 10H), 7.38 to 7.44 (m, 4H), 7.48 to 7.54 (m, 4H), 7.73 (s, 6H), 7.84 to 7.94 (m, 6H).

Compound Represented by Formula (2-1) Described Above:

A production process for the compound represented by Formula (2-1) described above shall be explained. Hereinafter, the present compound shall be called "ETM1".

A tetrahydrofuran solution 70 ml containing 0.55 g of lithium and 10 g of naphthalene was stirred at room temperature for 15 hours under argon flow to produce lithium naphthalinide. This solution was cooled at −20° C., and 30 ml of a tetrahydrofuran solution containing 6.9 g of dimethyl-bis(2,4,6-trimethyl-phenylethynyl)-silane was dropwise added thereto. Further, 4.6 ml of tert-butyl bromide was dropwise added, and then 12.6 g of zinc chloride tetramethylethylenediamine was added thereto. Subsequently, this solution was stirred at room temperature for 30 minutes, and then 11.2 g of 6-bromo-2,2'-bipyridine and 1.4 g of $PdCl_2(PPh_3)_2$ were added thereto and stirred at reflux temperature for 4.5 hours. After the reaction was finished, the above solution was cooled down to room temperature and concentrated by means of an evaporator. This concentrate was refined by column chromatography and recrystallization to obtain 9.2 g of the targeted compound.

The compound thus obtained had a melting point of 221° C. and a glass transition point (Tg) of 97° C. An NMR spectrum (δ (ppm), TMS) in deuterated chloroform was: σ=0.9 (s, 6H), 2.0 (s, 12H), 2.2 (s, 6H), 6.4 (s, 2H), 6.7 (s, 4H), 7.3 (m, 2H), 7.4 (t, 2H), 7.9 (t, 2H), 8.1 (d, 2H), 8.5 (d, 2H), 8.7 (d, 2H).

Compound Represented by Formula (2-2) Described Above:

A production process for the compound represented by Formula (2-2) described above shall be explained. Hereinafter, the present compound shall be called "ETM2".

A mixed solution of dioxane 220 ml containing 10.8 g of 6-bromo-2,2'-bipyridine, 5.6 g of anthracene-9,10-diboronic acid, 1.44 g of $Pd(PPh_3)_4$ and 17.7 g of tripotassium phosphate and 44 ml of water was stirred at reflux temperature for 17 hours under nitrogen flow. After the reaction was finished, the solution was cooled down to room temperature to thereby obtain a precipitate, and it was washed with a mixed solvent of methanol and water. Subsequently, the above precipitate was washed with ethyl acetate and then subjected to Soxhlet extraction with chloroform. The precipitate was filtered from the chloroform solution to obtain 6.5 g of the targeted compound.

The compound thus obtained had a melting point of 373° C. and a glass transition point (Tg) of 118° C. An NMR spectrum (δ (ppm), TMS) in deuterated chloroform was: σ=7.3 to 7.4 (m, 8H), 7.6 (m, 2H), 7.7 to 7.8 (m, 4H), 8.1 (t, 2H), 8.4 (d, 2H), 8.6 (m, 2H), 8.7 (m, 2H).

Compound Represented by Formula (5-1-1) Described Above:

A compound commercially available, for example, from Tokyo Kasei Kogyo Co., Ltd. can be used for the compound represented by Formula (5-1-1) described above. Hereinafter, the present compound shall be called "ETM3".

<Organic Electroluminescent Device>

Organic electroluminescent devices according to Examples 1 to 3 and organic electroluminescent devices according to Comparative Examples 1 to 4 were prepared, and measured respectively at current density set to 10 $mA/cm^2$ were voltage (V), luminance ($cd/m^2$), luminous efficiency (Lm/W) and life observed until initial luminance of 1000 $cd/m^2$ was reduced by half. The examples and the comparative examples shall be explained below in details.

The material compositions of the respective layers in the organic electroluminescent devices prepared according to Examples 1 to 3 and the organic electroluminescent devices prepared according to Comparative Examples 1 to 4 shall be shown in the following Table 1.

TABLE 1

| | Hole injection layer | Hole transport layer | Emission layer | | Electron transport layer |
|---|---|---|---|---|---|
| | | | Host | Dopant | |
| Example 1 | CuPc | NPD | BH | BD | ETM1 |
| Comparative Example 1 | CuPc | NPD | BH | BD-Ref | ETM1 |
| Comparative Example 2 | CuPc | NPD | BH | BD | ETM-Ref |
| Example 2 | CuPc | NPD | BH | BD | ETM2 |
| Comparative Example 3 | CuPc | NPD | BH | BD-Ref | ETM2 |
| Example 3 | CuPc | NPD | BH | BD | ETM3 |
| Comparative Example 4 | CuPc | NPD | BH | BD-Ref | ETM3 |

In Table 1, "CuPc" is copper phthalocyanine; "NPD" is N,N'-di(1-naphthyl)-N,N'-diphenylbenzidine; "BH" is 9-phenyl-10-[6-([1,1';3,1"]terphenyl-5'-yl)naphthalene-2-yl]anthracene; "BD" is 3,3'-(m-phenylene)bis(7-diphenylamino-coumarin); "BD-Ref" is 3,3'-(m-phenylene)bis(7-diethylamino-coumarin); "ETM1" is 2,5-bis(6'-(2',2"-bipyridyl)-1,1-dimethyl-3,4-dimesitylsilole; "ETM2" is 9,10-di(2',2"-bipyridyl)anthracene; "ETM3" is bathocuproine; and "ETM-Ref" is tris(8-quinolinolate)aluminum. The respective compounds have the following chemical structural formulas.

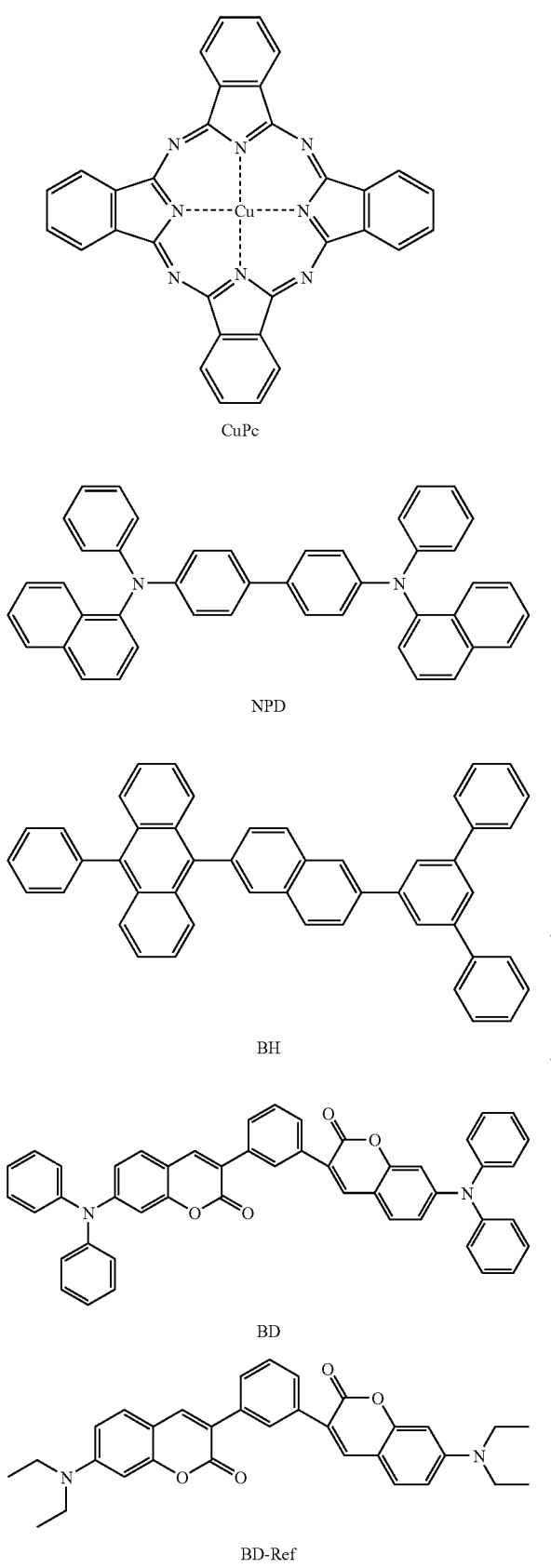

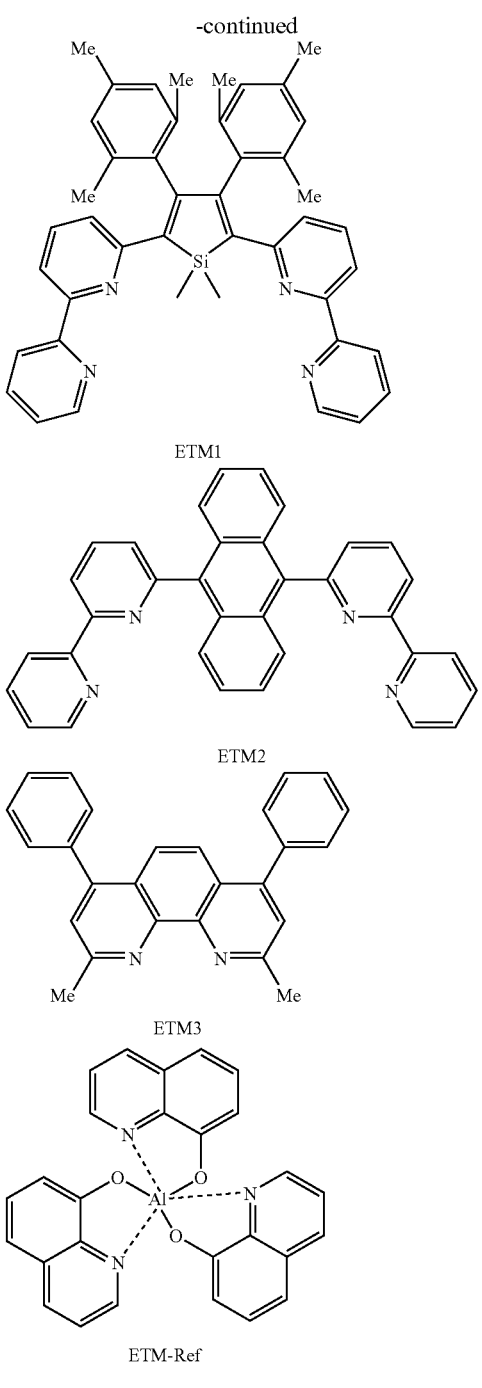

Example 1

ITO was deposited on a glass substrate in a thickness of 150 nm to prepare a transparent supporting substrate. This transparent supporting substrate was fixed on a substrate holder of a commercial deposition equipment, and loaded therein were a molybdenum-made boat for deposition containing "CuPc", a molybdenum-made boat for deposition containing "NPD", a molybdenum-made boat for deposition containing "BH", a molybdenum-made boat for deposition containing "BD", a molybdenum-made boat for deposition containing "ETM1", a molybdenum-made boat for deposition containing lithium fluoride and a tungsten-made boat for deposition containing aluminum.

The respective layers described below were formed in order on the ITO film of the transparent supporting substrate. A vacuum chamber was reduced in pressure up to $1 \times 10^{-3}$ Pa, and the boat for deposition containing "CuPc" was first heated to deposit it in a layer thickness of 20 nm, whereby a hole injection layer was formed. Then, the boat for deposition containing "NPD" was heated to deposit it in a layer thickness of 30 nm, whereby a hole transport layer was formed. Next, the boat for deposition containing "BH" and the boat for deposition containing "BD" were heated at the same time to deposit them in a layer thickness of 35 nm, whereby an emission layer was formed. The deposit rate was controlled so that a weight ratio of "BH" to "BD" was 95 to 5. Then, the boat for deposition containing "ETM1" was heated to deposit it in a layer thickness of 15 nm, whereby an electron transport layer was formed. The deposit rates of the respective layers were 0.001 to 3.0 nm/second.

Thereafter, the boat for deposition containing lithium fluoride was heated to deposit it at a deposit rate of 0.003 to 0.01 nm/second so that a layer thickness was 0.5 nm, and then the boat for deposition containing aluminum was heated to deposit it at a deposit rate of 0.1 to 1 nm/second so that a layer thickness was 100 nm, whereby a cathode was formed. Thus, an organic electroluminescent device was obtained.

With the ITO electrode set to an anode and the lithium fluoride/aluminum electrode set to a cathode, the characteristics were measured at a current density set to 10 mA/cm$^2$ to find that the voltage was 4.14 (V); the luminance was 930 (cd/m$^2$); the luminous efficiency was 7.05 (Lm/W); and the life observed until an initial luminance of 1000 cd/m$^2$ was reduced by half was 1000 hours or longer.

Comparative Example 1

An organic electroluminescent device was obtained in the same manner as in Example 1, except that "BD-Ref" was used in place of "BD" which was the emission layer material (dopant) used in Example 1. With the ITO electrode set to an anode and the lithium fluoride/aluminum electrode set to a cathode, the characteristics were measured at a current density set to 10 mA/cm$^2$ to find that the voltage was 3.80 (V); the luminance was 640 (cd/m$^2$); the luminous efficiency was 5.29 (Lm/W); and the life observed until an initial luminance of 1000 cd/m$^2$ was reduced by half was 170 hours.

Comparative Example 2

An organic electroluminescent device was obtained in the same manner as in Example 1, except that "ETM-Ref" was used in place of "ETM1" which was the electron transport layer material used in Example 1. With the ITO electrode set to an anode and the lithium fluoride/aluminum electrode set to a cathode, the characteristics were measured at a current density set to 10 mA/cm$^2$ to find that the voltage was 6.10 (V); the luminance was 510 (cd/m$^2$); the luminous efficiency was 2.63 (Lm/W); and the life observed until an initial luminance of 1000 cd/m$^2$ was reduced by half was 600 hours.

Example 2

An organic electroluminescent device was obtained in the same manner as in Example 1, except that "ETM2" was used in place of "ETM1" which was the electron transport layer material used in Example 1. With the ITO electrode set to an anode and the lithium fluoride/aluminum electrode set to a cathode, the characteristics were measured at a current density set to 10 mA/cm$^2$ to find that the voltage was 3.95 (V); the luminance was 870 (cd/m$^2$); the luminous efficiency was 6.92 (Lm/W); and the life observed until an initial luminance of 1000 cd/m$^2$ was reduced by half was 600 hours.

Comparative Example 3

An organic electroluminescent device was obtained in the same manner as in Example 2, except that "BD-Ref" was used in place of "BD" which was the emission layer material (dopant) used in Example 2. With the ITO electrode set to an anode and the lithium fluoride/aluminum electrode set to a cathode, the characteristics were measured at a current density set to 10 mA/cm$^2$ to find that the voltage was 3.70 (V); the luminance was 510 (cd/m$^2$); the luminous efficiency was 4.33 (Lm/W); and the life observed until an initial luminance of 1000 cd/m$^2$ was reduced by half was 100 hours.

Example 3

An organic electroluminescent device was obtained in the same manner as in Example 1, except that "ETM3" was used in place of "ETM1" which was the electron transport layer material used in Example 1. With the ITO electrode set to an anode and the lithium fluoride/aluminum electrode set to a cathode, the characteristics were measured at a current density set to 10 mA/cm$^2$ to find that the voltage was 7.00 (V); the luminance was 635 (cd/m$^2$); the luminous efficiency was 2.85 (Lm/W); and the life observed until an initial luminance of 1000 cd/m$^2$ was reduced by half was 130 hours.

Comparative Example 4

An organic electroluminescent device was obtained in the same manner as in Example 3, except that "BD-Ref" was used in place of "BD" which was the emission layer material (dopant) used in Example 3. With the ITO electrode set to an anode and the lithium fluoride/aluminum electrode set to a cathode, the characteristics were measured at a current density set to 10 mA/cm$^2$ to find that the voltage was 6.60 (V); the luminance was 420 (cd/m$^2$); the luminous efficiency was 2.00 (Lm/W); and the life observed until an initial luminance of 1000 cd/m$^2$ was reduced by half was 40 hours.

TABLE 2

| | Characteristics at a current density of 10 mA/cm$^2$ | | | Initial |
| --- | --- | --- | --- | --- |
| | Voltage V | Luminance cd/m$^2$ | Luminous efficiency Lm/W | 1000 cd/m$^2$ Life hours |
| Example 1 | 4.14 | 930 | 7.05 | 1000 or more |
| Comparative Example 1 | 3.80 | 640 | 5.29 | 170 |
| Comparative Example 2 | 6.10 | 510 | 2.63 | 600 |
| Example 2 | 3.95 | 870 | 6.92 | 600 |
| Comparative Example 3 | 3.70 | 510 | 4.33 | 100 |
| Example 3 | 7.00 | 635 | 2.85 | 130 |
| Comparative Example 4 | 6.60 | 420 | 2.00 | 40 |

INDUSTRIAL APPLICABILITY

According to the preferred embodiment of the present invention, capable of being provided are an organic electroluminescent device having better performances in luminous efficiency, device life and driving voltage, a display unit equipped with the same, a lighting instrument equipped with the same and the like.

What is claimed is:

1. An organic electroluminescent device comprising a pair of electrodes comprising an anode and a cathode and at least one organic compound layer containing an emission layer disposed between a pair of the above electrodes, wherein the emission layer contains at least one of a compound represented by the following Formula (1):

$$\phi(Z)_m \qquad (1)$$

(in Formula (1), φ represents a benzene ring or a pyridine ring of an m valence which may be substituted; Z represents a coumarin residue represented by the following Formula (1-Z) which is bonded to φ described above and which may be the same as or different from each other; and m is 2 or 3)

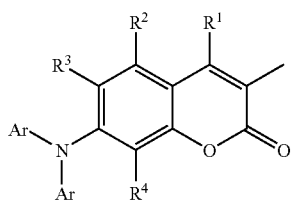

(1-Z)

(in Formula (1-Z), $R^1$, $R^2$, $R^3$ and $R^4$ each represent independently hydrogen, alkyl which may be substituted, alkenyl which may be substituted, alkynyl which may be substituted, alkoxy which may be substituted, alkylthio which may be substituted, aryl which may be substituted, aryloxy which may be substituted, arylthio which may be substituted, arylalkyl which may be substituted, arylalkoxy which may be substituted, arylalkylthio which may be substituted, arylalkenyl which may be substituted, arylalkynyl which may be substituted, arylsulfonyloxy which may be substituted, alkylsulfonyloxy which may be substituted, heteroaryl which may be substituted, cycloalkyl which may be substituted, halogen, cyano, nitro or hydroxyl;

Ar each represents independently aryl which may be substituted or heteroaryl which may be substituted; and $R^1$ and $R^2$, or $R^2$ and $R^3$ may be bonded to each other to form a ring.

2. The organic electroluminescent device as described in claim 1, wherein $R^1$, $R^2$, $R^3$ and $R^4$ each represent independently hydrogen, alkyl which may be substituted, alkenyl which may be substituted, alkynyl which may be substituted, aryl which may be substituted, arylthio which may be substituted, arylalkyl which may be substituted, heteroaryl which may be substituted, cycloalkyl which may be substituted, halogen or cyano.

3. The organic electroluminescent device as described in claim 1, wherein φ may be substituted with alkyl having 1 to 4 carbon atoms, cyanomethyl, phenyl, naphthyl, methylphenyl, ethylphenyl, methylnaphthyl, ethylnaphthyl, pyridyl, benzothiazolyl or indanyl;

$R^1$ is hydrogen, alkyl having 1 to 6 carbon atoms, alkenyl having 2 to 6 carbon atoms, alkynyl having 2 to 6 carbon atoms, aryl having 6 to 20 carbon atoms or cyano;

$R^2$, $R^3$ and $R^4$ each represent independently hydrogen, alkyl having 1 to 6 carbon atoms, phenylthio, halogen, or alkyl having 1 to 6 carbon atoms which is substituted with phenyl or naphthyl; and Ar each represents independently aryl having 6 to 20 carbon atoms or heteroaryl having 2 to 20 carbon atoms, and hydrogen of the above aryl or heteroaryl each may be independently replaced by alkyl having 1 to 4 carbon atoms, halogenated alkyl having 1 to 4 carbon atoms, alkoxy having 1 to 4 carbon atoms, phenyl, halogen or cyano.

4. The organic electroluminescent device as described in claim 1, wherein φ may be substituted with alkyl having 1 to 4 carbon atoms, phenyl, cyanomethyl, pyridyl, benzothiazol-2-yl or indan-1-yl;

$R^1$ is hydrogen or alkyl having 1 to 4 carbon atoms;

$R^2$, $R^3$ and $R^4$ each represent independently hydrogen, alkyl having 1 to 4 carbon atoms, phenylthio, halogen, or alkyl having 1 to 4 carbon atoms which is substituted with naphthyl; and Ar each represents independently phenyl, perfluorophenyl, tolyl, xylyl, p-t-butylphenyl, biphenylyl, naphthyl, quinolinyl, anthracenyl, phenanthryl, terphenylyl, fluorenyl, pyrenyl, cyanophenyl, perfluoromethylphenyl, or 4-alkoxyphenyl in which alkoxy is having 1 to 4 carbon atoms and hydrogen of phenyl each may be independently replaced by halogen.

5. The organic electroluminescent device as described in claim 1, wherein the compound is represented by the following Formula (1-1), (1-2), (1-3), (1-4), (1-5), (1-6), (1-7), (1-9), (1-10), (1-11), (1-13), (1-15), (1-18), (1-19), (1-23) or (1-25):

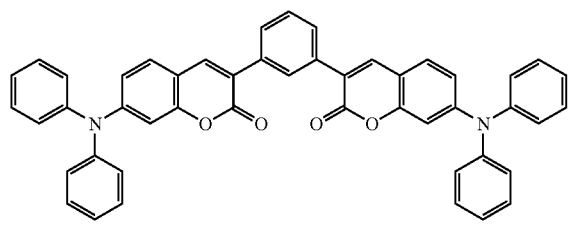

(1-1)

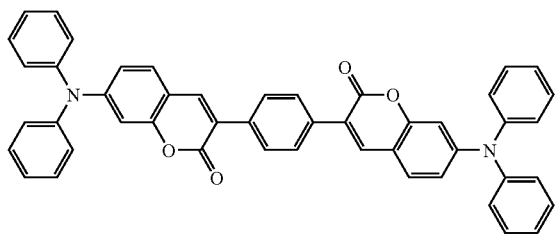

(1-2)

-continued
(1-3)
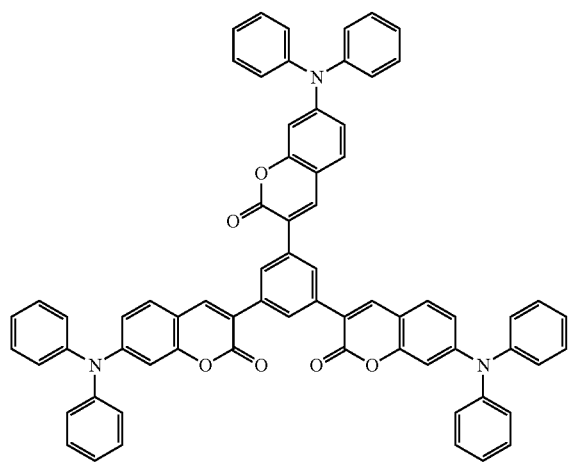
(1-4)
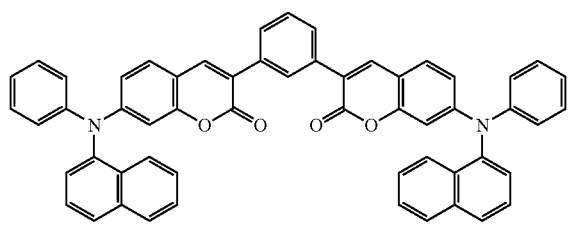
(1-5)
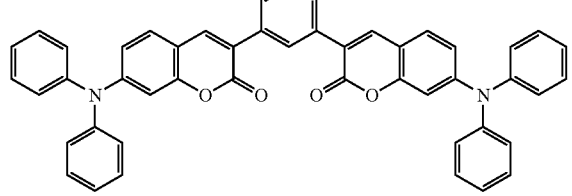
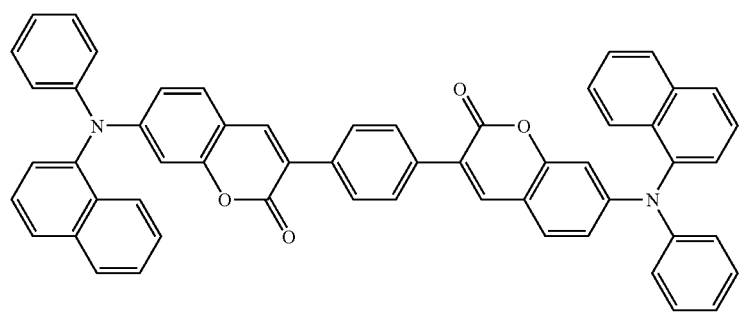
(1-6)
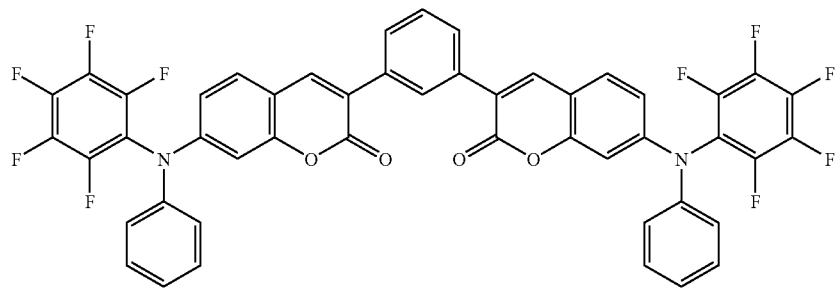
(1-7)
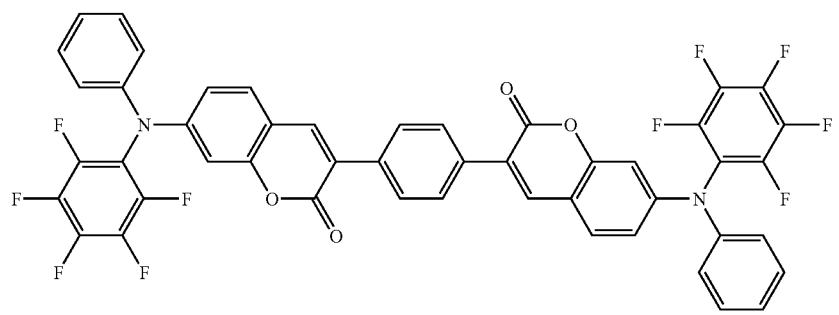

-continued
(1-9)
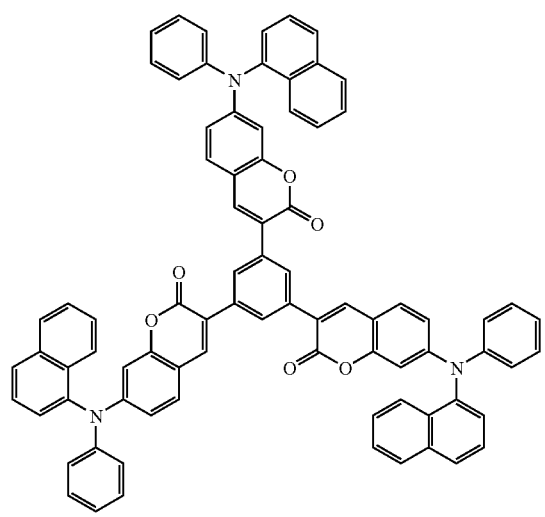
(1-10)
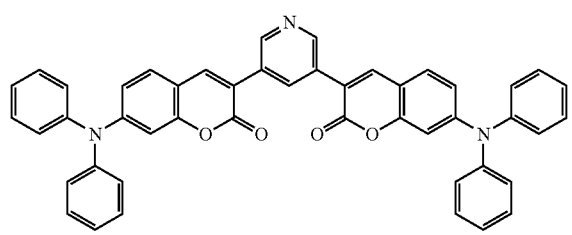
(1-11)
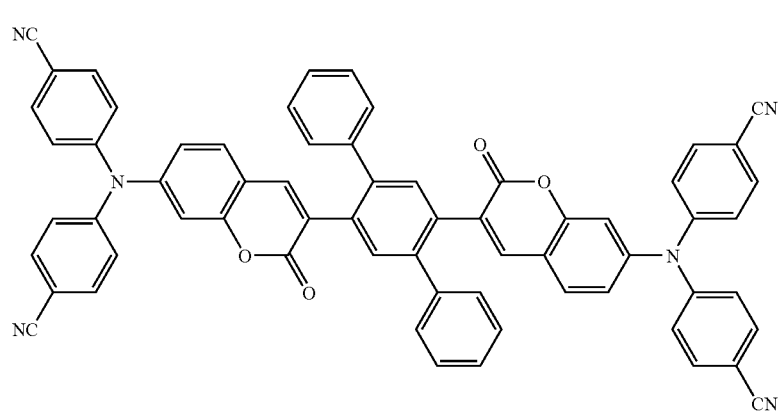
(1-13)
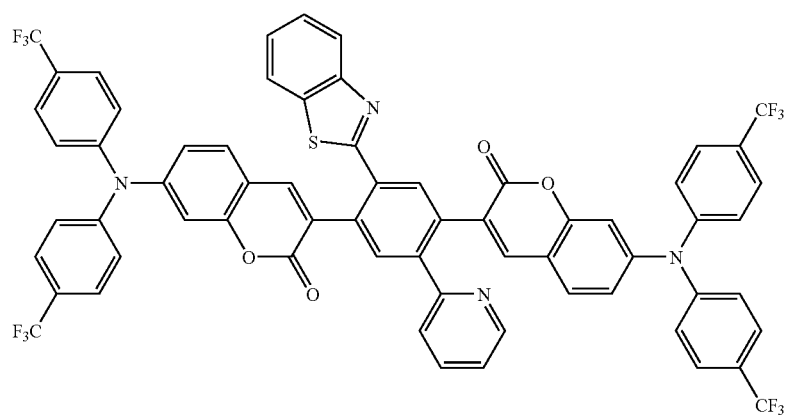

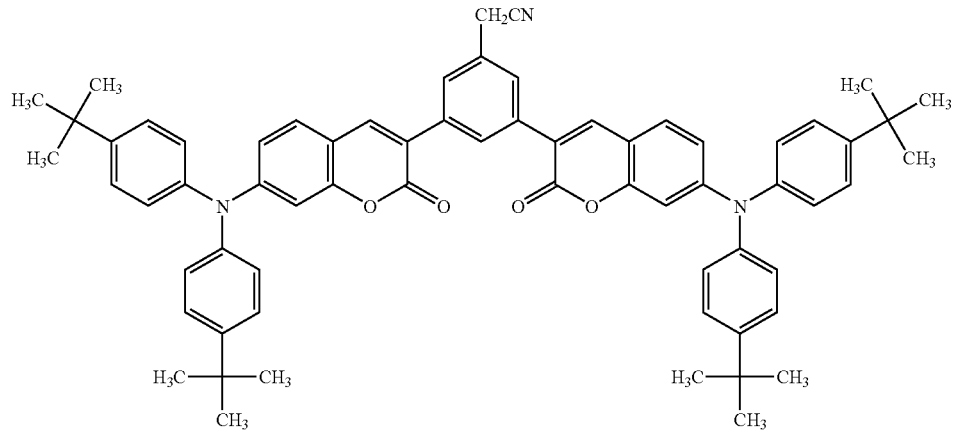
(1-15)
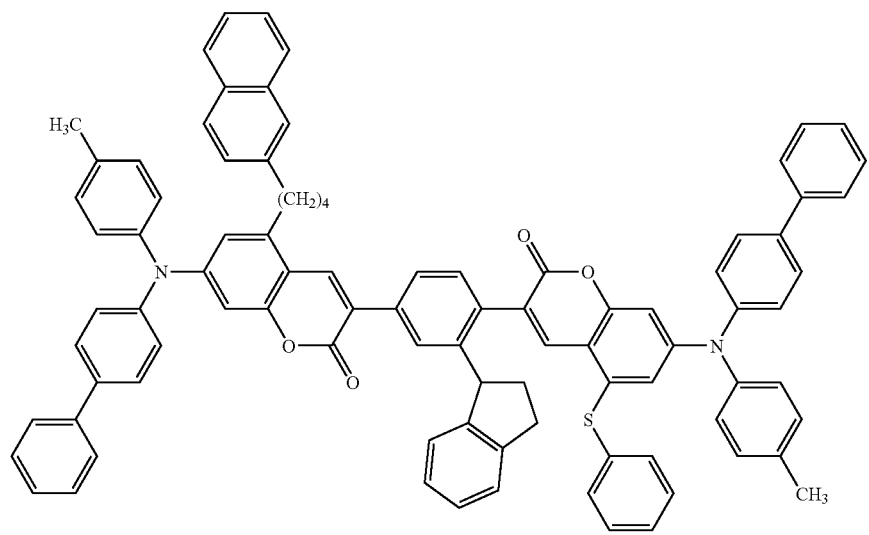
(1-18)
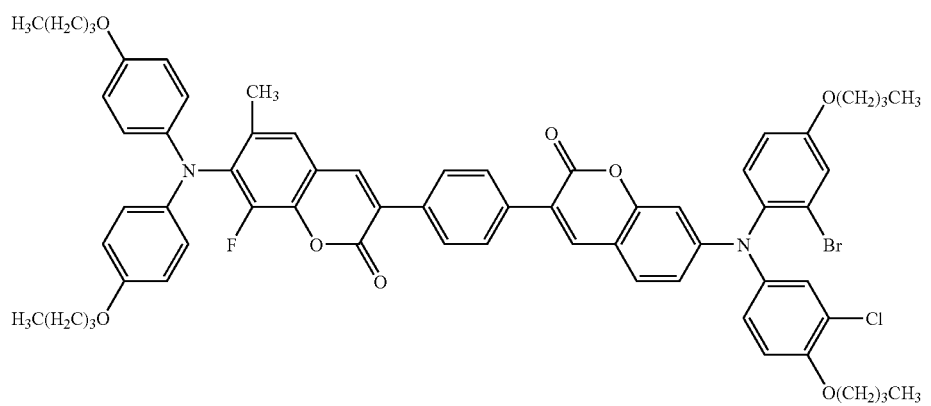
(1-19)

-continued (1-23)

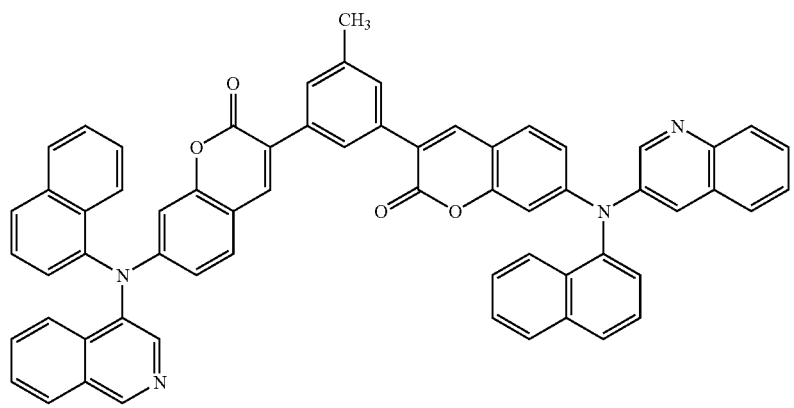

(1-25)

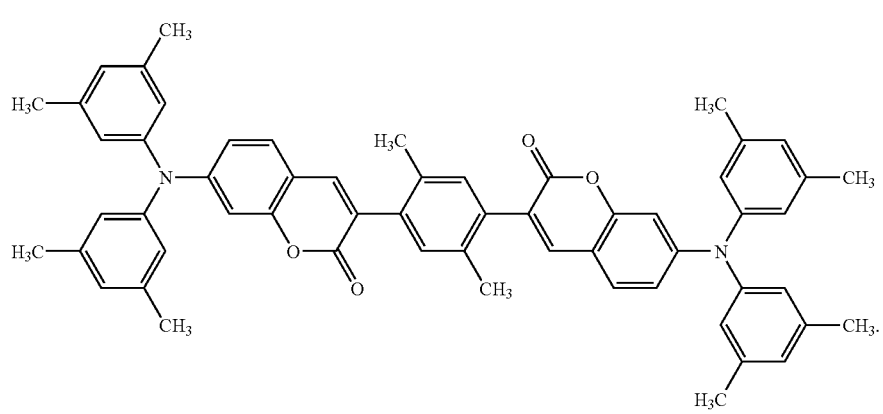

6. The organic electroluminescent device as described in claim 1, further comprising an electron transport layer containing at least one of compounds represented by the following Formula (2) between the cathode and the emission layer each described above:

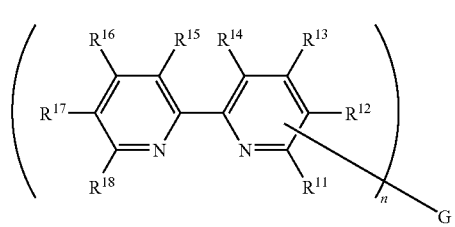

(2)

(in Formula (2),

G represents a mere bond or a linkage group of an n valence;

n is 2, 3, 4, 5, 6, 7 or 8;

$R^{11}$, $R^{12}$, $R^{13}$, $R^{14}$, $R^{15}$, $R^{16}$, $R^{17}$ and $R^{18}$ each represent independently hydrogen, alkyl which may be substituted, alkenyl which may be substituted, aryl which may be substituted, arylalkyl which may be substituted, arylalkenyl which may be substituted, boryl which may be substituted, silyl which may be substituted, aralkyl which may be substituted, heteroaryl which may be substituted, cycloalkyl which may be substituted or cyano, and adjacent groups may be combined with each other to form a condensed ring(s);

at least one of $R^{11}$, $R^{12}$, $R^{13}$, $R^{14}$, $R^{15}$, $R^{16}$, $R^{17}$ and $R^{18}$ represents G, and n groups of a 2,2'-bipyridyl residue formed by $R^{11}$, $R^{12}$, $R^{13}$, $R^{14}$, $R^{15}$, $R^{16}$, $R^{17}$ and $R^{18}$ and a 2,2'-bipyridyl nucleus may be the same as or different from each other).

7. The organic electroluminescent device as described in claim 6, wherein G represents an aromatic group or a heteroaromatic group of an n valence which is constituted by one or plural five-membered rings or six-membered rings and which may be substituted;

n is 2, 3, 4, 5 or 6;

$R^{11}$, $R^{12}$, $R^{13}$, $R^{14}$, $R^{15}$, $R^{16}$, $R^{17}$ and $R^{18}$ each represent independently hydrogen, alkyl having 1 to 20 carbon atoms which may be substituted, alkenyl having 2 to 20 carbon atoms which may be substituted, aryl having 5 to 30 carbon atoms which may be substituted, arylalkyl having 6 to 30 carbon atoms which may be substituted, arylalkenyl having 6 to 30 carbon atoms which may be substituted, arylboryl, alkylsilyl, aralkyl having 7 to 20 carbon atoms which may be substituted, heteroaryl having 2 to 30 carbon atoms which may be substituted, cycloalkyl having 3 to 10 carbon atoms which may be substituted or cyano; and the substituent in G, $R^{11}$, $R^{12}$, $R^{13}$, $R^{14}$, $R^{15}$, $R^{16}$, $R^{17}$ and $R^{18}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

8. The organic electroluminescent device as described in claim 6, wherein G represents an aromatic group or a heteroaromatic group of an n valence which is constituted by one or plural five-membered rings or six-membered rings and which may be substituted, and they may be substituted with alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl;

n is 2, 3 or 4; and $R^{11}$, $R^{12}$, $R^{13}$, $R^{14}$, $R^{15}$, $R^{16}$, $R^{17}$ and $R^{18}$ each represent independently hydrogen, alkyl having 1 to 12 carbon atoms, alkenyl having 2 to 12 carbon atoms, aryl having 5 to 25 carbon atoms, diarylboryl, trialkylsilyl, aralkyl having 7 to 15 carbon atoms, cycloalkyl having 3 to 8 carbon atoms or cyano.

9. The organic electroluminescent device as described in claim 6, wherein G represents a benzene ring, a naphthalene ring, an anthracene ring, a phenanthrene ring, a fluorene ring, a terphenyl ring, a biphenyl ring, a thiophene ring, a pyridine ring, a pyrazine ring, a pyrimidine ring, a phenalene ring, a silole ring or a pyridazine ring each having an n valence, and the above rings may be substituted with alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl;

n is 2 or 3; and $R^{11}$, $R^{12}$, $R^{13}$, $R^{14}$, $R^{15}$, $R^{16}$, $R^{17}$ and $R^{18}$ each represent independently hydrogen, alkyl having 1 to 6 carbon atoms, alkenyl having 2 to 6 carbon atoms or aryl having 5 to 20 carbon atoms.

10. The organic electroluminescent device as described in claim 6, wherein G represents a benzene ring, a naphthalene ring, an anthracene ring, a phenanthrene ring, a fluorene ring, a thiophene ring, a pyridine ring, a phenalene ring or a silole ring each having an n valence, and the above rings may be substituted with alkyl having 1 to 4 carbon atoms, phenyl, tolyl, xylyl, mesityl, naphthyl, ethylphenyl, methylnaphthyl, ethylnaphthyl or pyridyl;

n is 2 or 3; and $R^{11}$, $R^{12}$, $R^{13}$, $R^{14}$, $R^{15}$, $R^{16}$, $R^{17}$ and $R^{18}$ each represent independently hydrogen, alkyl having 1 to 4 carbon atoms, phenyl, tolyl or xylyl.

11. The organic electroluminescent device as described in claim 6, wherein the electron transport layer contains a compound represented by the following Formula (2-1) or Formula (2-2):

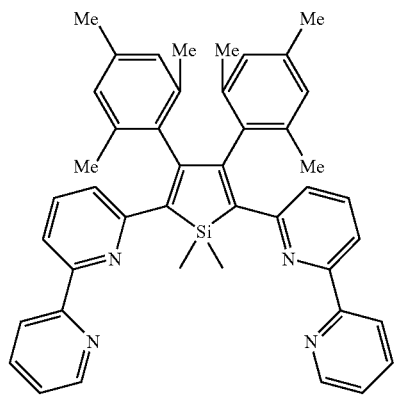

(2-1)

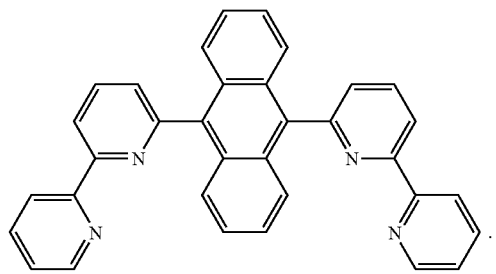

(2-2)

12. The organic electroluminescent device as described in claim 1, further comprising an electron transport layer containing at least one of compounds represented by the following Formula (3) between the cathode and the emission layer each described above:

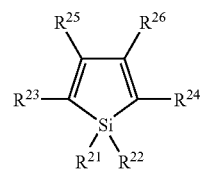

(3)

(in Formula (3), $R^{21}$, $R^{22}$, $R^{25}$ and $R^{26}$ each represent independently hydrogen, alkyl which may be substituted, alkenyl which may be substituted, aryl which may be substituted, arylalkyl which may be substituted, silyl which may be substituted, aralkyl which may be substituted, heteroaryl which may be substituted, cycloalkyl which may be substituted or cyano; and $R^{23}$ and $R^{24}$ each represent independently aryl which may be substituted or heteroaryl which may be substituted).

13. The organic electroluminescent device as described in claim 12, wherein $R^{21}$, $R^{22}$, $R^{25}$ and $R^{26}$ each represent independently hydrogen, alkyl having 1 to 20 carbon atoms which may be substituted, alkenyl having 2 to 20 carbon atoms which may be substituted, aryl having 5 to 30 carbon atoms which may be substituted, arylalkyl having 6 to 30 carbon atoms which may be substituted, alkylsilyl, aralkyl having 7 to 20 carbon atoms which may be substituted, heteroaryl having 2 to 30 carbon atoms which may be substituted, cycloalkyl having 3 to 10 carbon atoms which may be substituted or cyano;

$R^{23}$ and $R^{24}$ each represent independently heteroaryl having 2 to 30 carbon atoms which may be substituted; and the substituent in $R^{21}$, $R^{22}$, $R^{23}$, $R^{24}$, $R^{25}$ and $R^{26}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

14. The organic electroluminescent device as described in claim 12, wherein $R^{21}$ and $R^{22}$ each represent independently phenyl, naphthyl, alkyl having 1 to 6 carbon atoms or cycloalkyl having 3 to 8 carbon atoms;

$R^{25}$ and $R^{26}$ each represent independently aryl having 5 to 20 carbon atoms which may be substituted or heteroaryl having 2 to 20 carbon atoms which may be substituted;

the substituent in $R^{25}$ and $R^{26}$ is alkyl having 1 to 4 carbon atoms, phenyl, tolyl, xylyl, mesityl, naphthyl, methylnaphthyl, pyridyl or quinolyl;

$R^{23}$ and $R^{24}$ each represent independently heteroaryl having 2 to 20 carbon atoms which may be substituted; and the substituent in $R^{23}$ and $R^{24}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

15. The organic electroluminescent device as described in claim 12, wherein $R^{21}$ and $R^{22}$ each represent phenyl, naphthyl, alkyl having 1 to 4 carbon atoms or cycloalkyl having 3 to 6 carbon atoms;

$R^{25}$ and $R^{26}$ each independently phenyl, tolyl, xylyl, mesityl, naphthyl, quinolinyl or pyridyl, and they may be substituted with alkyl having 1 to 4 carbon atoms, phenyl, tolyl, xylyl, mesityl, naphthyl, methylnaphthyl, pyridyl or quinolyl;

$R^{23}$ and $R^{24}$ each represent independently phenanthrolinyl, quinolyl, pyridyl, pyrimidinyl, pyrazinyl, pyridazinyl, thienyl, thiazolyl, triazolyl, oxazolyl, oxadiazolyl, imidazolyl, benzoxazolyl, benzothiazolyl, benzothienyl, carbazolyl or thiazolyl, and they may be substituted with phenyl, pyridyl, pyrimidinyl, pyrazinyl, pyridazinyl, imidazolyl, quinolyl, phenanthrolinyl, benzothiazolyl or benzothienyl.

16. The organic electroluminescent device as described in claim 1, further comprising an electron transport layer containing at least one of compounds represented by the following Formula (4) between the cathode and the emission layer each described above:

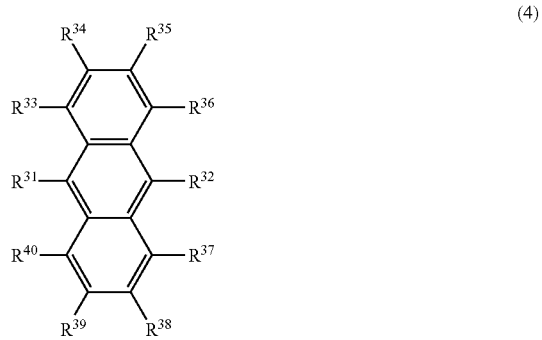

(in Formula (4), $R^{31}$ and $R^{32}$ each represent independently heteroaryl which may be substituted;

$R^{33}$, $R^{34}$, $R^{35}$, $R^{36}$, $R^{37}$, $R^{38}$, $R^{39}$ and $R^{40}$ each represent independently hydrogen, alkyl which may be substituted, aryl which may be substituted, boryl which may be substituted, silyl which may be substituted, aralkyl which may be substituted, heteroaryl which may be substituted, cycloalkyl which may be substituted or cyano, and adjacent groups may be combined with each other to form a condensed ring(s)).

17. The organic electroluminescent device as described in claim 16, wherein $R^{31}$ and $R^{32}$ each represent independently heteroaryl having 2 to 30 carbon atoms which may be substituted;

$R^{33}$, $R^{34}$, $R^{35}$, $R^{36}$, $R^{37}$, $R^{38}$, $R^{39}$ and $R^{40}$ each represent independently hydrogen, alkyl having 1 to 20 carbon atoms which may be substituted, aryl having 5 to 30 carbon atoms which may be substituted, arylboryl, alkylsilyl, aralkyl having 7 to 20 carbon atoms which may be substituted, heteroaryl having 2 to 30 carbon atoms which may be substituted, cycloalkyl having 3 to 10 carbon atoms which may be substituted or cyano; and the substituent in $R^{31}$, $R^{32}$, $R^{33}$, $R^{34}$, $R^{35}$, $R^{36}$, $R^{37}$, $R^{38}$, $R^{39}$ and $R^{40}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

18. The organic electroluminescent device as described in claim 16, wherein $R^{31}$ and $R^{32}$ each represent independently heteroaryl having 2 to 25 carbon atoms which may be substituted;

the substituent in $R^{31}$ and $R^{32}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl; and $R^{33}$, $R^{34}$, $R^{35}$, $R^{36}$, $R^{37}$, $R^{38}$, $R^{39}$ and $R^{40}$ each represent independently hydrogen, alkyl having 1 to 12 carbon atoms, aryl having 5 to 25 carbon atoms, diarylboryl, trialkylsilyl, aralkyl having 7 to 15 carbon atoms, cycloalkyl having 3 to 8 carbon atoms or cyano.

19. The organic electroluminescent device as described in claim 16, wherein $R^{31}$ and $R^{32}$ each represent independently pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl, and they may be substituted with pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl; and $R^{33}$, $R^{34}$, $R^{35}$, $R^{36}$, $R^{37}$, $R^{38}$, $R^{39}$ and $R^{40}$ each represent independently hydrogen, alkyl having 1 to 4 carbon atoms, phenyl, tolyl or xylyl.

20. The organic electroluminescent device as described in claim 1, further comprising an electron transport layer containing at least one of compounds represented by the following Formula (5-1) or (5-2) between the cathode and the emission layer each described above:

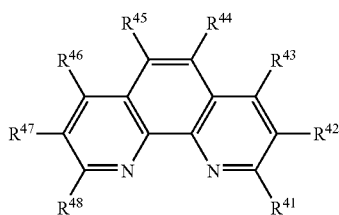

(5-1)

(in Formula (5-1), $R^{41}$, $R^{42}$, $R^{43}$, $R^{44}$, $R^{45}$, $R^{46}$, $R^{47}$ and $R^{48}$ each represent independently hydrogen, alkyl which may be substituted, alkenyl which may be substituted, aryl which may be substituted, arylalkyl which may be substituted, boryl which may be substituted, silyl which may be substituted, aralkyl which may be substituted, heteroaryl which may be substituted, cycloalkyl which may be substituted or cyano, and adjacent groups may be combined with each other to form a condensed ring(s));

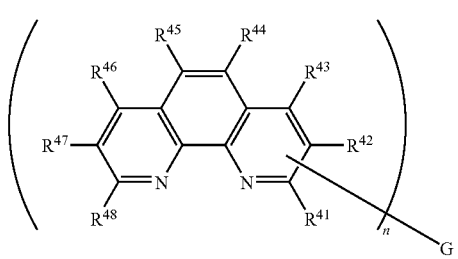

(5-2)

(in Formula (5-2), G represents a mere bond or a linkage group of an n valence;

n is 2, 3, 4, 5, 6, 7 or 8;

$R^{41}$, $R^{42}$, $R^{43}$, $R^{44}$, $R^{45}$, $R^{46}$, $R^{47}$ and $R^{48}$ each represent independently hydrogen, alkyl which may be substituted, alkenyl which may be substituted, aryl which may be substituted, arylalkyl which may be substituted, boryl which may be substituted, silyl which may be substituted, aralkyl which may be substituted, heteroaryl which may be substituted, cycloalkyl which may be substituted or cyano, and adjacent groups may be combined with each other to form a condensed ring(s);

at least one of $R^{41}$, $R^{42}$, $R^{43}$, $R^{44}$, $R^{45}$, $R^{46}$, $R^{47}$ and $R^{48}$ represents G, and n groups of a phenanthroline residue formed by $R^{41}$, $R^{42}$, $R^{43}$, $R^{44}$, $R^{45}$, $R^{46}$, $R^{47}$ and $R^{48}$ and a phenanthroline nucleus may be the same as or different from each other).

21. The organic electroluminescent device as described in claim 20, wherein G represents an aromatic group or a heteroaromatic group of an n valence which is constituted by one or plural five-membered rings or six-membered rings and which may be substituted;

n is 2, 3, 4, 5 or 6;

$R^{41}$, $R^{42}$, $R^{43}$, $R^{44}$, $R^{45}$, $R^{46}$, $R^{47}$ and $R^{48}$ each represent independently hydrogen, alkyl having 1 to 20 carbon atoms which may be substituted, alkenyl having 2 to 20 carbon atoms which may be substituted, aryl having 5 to 30 carbon atoms which may be substituted, arylalkyl having 6 to 30 carbon atoms which may be substituted, arylboryl, alkylsilyl, aralkyl having 7 to 20 carbon atoms which may be substituted, heteroaryl having 2 to 30 carbon atoms which may be substituted, cycloalkyl having 3 to 10 carbon atoms which may be substituted or cyano; and the substituent in G, $R^{41}$, $R^{42}$, $R^{43}$, $R^{44}$, $R^{45}$, $R^{46}$, $R^{47}$ and $R^{48}$ is alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, oxazolyl, oxadiazolyl, quinolyl, phenanthrolinyl, benzoxazolyl, benzothiazolyl, benzothienyl or carbazolyl.

22. The organic electroluminescent device as described in claim 20, wherein G represents an aromatic group or a heteroaromatic group of an n valence which is constituted by one or plural five-membered rings or six-membered rings and which may be substituted, and they may be substituted with alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl;

n is 2, 3 or 4; and $R^{41}$, $R^{42}$, $R^{43}$, $R^{44}$, $R^{45}$, $R^{46}$, $R^{47}$ and $R^{48}$ each represent independently hydrogen, alkyl having 1 to 12 carbon atoms, alkenyl having 2 to 12 carbon atoms, aryl having 5 to 25 carbon atoms, diarylboryl, trialkylsilyl, aralkyl having 7 to 15 carbon atoms, cycloalkyl having 3 to 8 carbon atoms or cyano.

23. The organic electroluminescent device as described in claim 20, wherein G represents a benzene ring, a naphthalene ring, an anthracene ring, a phenanthrene ring, a fluorene ring, a terphenyl ring, a biphenyl ring, a thiophene ring, a pyridine ring, a pyrazine ring, a pyrimidine ring, a phenalene ring, a silole ring or a pyridazine ring each having an n valence, and the above rings may be substituted with alkyl having 1 to 4 carbon atoms, phenyl, tolyl, xylyl, mesityl, naphthyl, ethylphenyl, methylnaphthyl, ethylnaphthyl, pyridyl, pyrimidinyl, pyrazinyl, pyridazinyl, thienyl, imidazolyl, thiazolyl, triazolyl, quinolyl, phenanthrolinyl, benzothiazolyl, benzothienyl or carbazolyl;

n is 2 or 3; and $R^{41}$, $R^{42}$, $R^{43}$, $R^{44}$, $R^{45}$, $R^{46}$, $R^{47}$ and $R^{48}$ each represent independently hydrogen, alkyl having 1 to 6 carbon atoms, alkenyl having 2 to 6 carbon atoms or aryl having 5 to 20 carbon atoms.

24. The organic electroluminescent device as described in claim 20, wherein G represents a benzene ring, a naphthalene ring, an anthracene ring, a phenanthrene ring, a fluorene ring, a thiophene ring, a pyridine ring, a phenalene ring or a silole ring each having an n valence, and the above rings may be substituted with alkyl having 1 to 4 carbon atoms, phenyl, tolyl, xylyl, mesityl, naphthyl, ethylphenyl, methylnaphthyl, ethylnaphthyl or pyridyl;

n is 2 or 3; and $R^{41}$, $R^{42}$, $R^{43}$, $R^{44}$, $R^{45}$, $R^{46}$, $R^{47}$ and $R^{48}$ each represent independently hydrogen, alkyl having 1 to 4 carbon atoms, phenyl, tolyl or xylyl.

25. The organic electroluminescent device as described in claim 20, wherein the electron transport layer contains a compound represented by the following Formula (5-1-1):

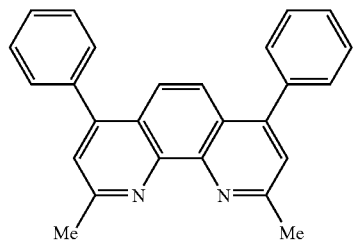

(5-1-1)

26. A display unit comprising the organic electroluminescent device as described in any of claims 1-5 or 6-25.

27. A lighting instrument comprising the organic electroluminescent device as described in any of claims 1-5 or 6-25.

* * * * *